United States Patent
Jarman et al.

(10) Patent No.: US 11,702,546 B2
(45) Date of Patent: Jul. 18, 2023

(54) NEAR-INFRARED HEPTAMETHINE DYES FOR GENERATION OF SINGLET OXYGEN

(71) Applicant: California Institute of Technology, Pasadena, CA (US)

(72) Inventors: John B. Jarman, Pasadena, CA (US); Dennis A. Dougherty, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 676 days.

(21) Appl. No.: 16/661,535

(22) Filed: Oct. 23, 2019

(65) Prior Publication Data

US 2020/0131370 A1 Apr. 30, 2020

Related U.S. Application Data

(60) Provisional application No. 62/750,095, filed on Oct. 24, 2018.

(51) Int. Cl.
*C09B 23/08* (2006.01)
*A61N 5/06* (2006.01)

(52) U.S. Cl.
CPC ............ *C09B 23/086* (2013.01); *A61N 5/062* (2013.01); *A61N 2005/0659* (2013.01)

(58) Field of Classification Search
CPC ............................ C07D 309/16; C07D 335/02
See application file for complete search history.

(56) References Cited

U.S. PATENT DOCUMENTS

| | | |
|---|---|---|
| 4,283,475 A | 8/1981 | Kawamura et al. |
| 4,464,383 A | 8/1984 | Yamamoto |
| 5,563,028 A | 10/1996 | Nakamura et al. |
| 5,633,390 A | 5/1997 | Nakamura et al. |
| 5,973,158 A | 10/1999 | Usami et al. |
| 6,072,059 A | 6/2000 | Harada et al. |
| 6,515,811 B2 | 2/2003 | Ikuhara et al. |
| 6,673,943 B2 | 1/2004 | Waggoner et al. |
| 7,727,544 B2 | 6/2010 | Schwartz et al. |
| 8,414,911 B2 | 4/2013 | Mattson et al. |
| 8,735,601 B2 | 5/2014 | Peng et al. |
| 8,889,887 B2 | 11/2014 | Peng et al. |
| 9,452,172 B2 | 9/2016 | Scherz et al. |
| 9,610,370 B2 | 4/2017 | Chung et al. |
| 10,280,307 B2 | 5/2019 | Schnermann et al. |
| 2008/0048155 A1 | 2/2008 | Toriniwa et al. |
| 2010/0166659 A1 | 7/2010 | Licha et al. |
| 2011/0111515 A1 | 5/2011 | Nagano et al. |
| 2014/0210034 A1 | 7/2014 | Huang et al. |
| 2018/0200389 A1 | 7/2018 | Wong et al. |

FOREIGN PATENT DOCUMENTS

WO 2018/191363 A1 10/2018

OTHER PUBLICATIONS

Castro et al., "Perfluorocarbon-Based Oxygen Carriers: Review of Products and Trials", Artificial Organs, 2010, 34(8), 622-634.
Riess et al., "Perfluoro Compounds as Blood Substitutes", Angew. Chem., 1978, 17, (9), 621-700.
Tan et al., "NIR Heptamethine dye with intrinsic cancer targeting, imaging and photosensitizing properties", Biomaterials, 2012, vol. 33, pp. 2230-2239.
Jarman, J. B. et al., "Charge-transfer heptamethine dyes for NIR singlet oxygen generation", Chemical Communications, 2019, vol. 55, pp. 5511-5514.
Jiao, L. et al., "A near-infrared heptamethine aminocyanine dye with a long-lived excited triplet state for photodynamic therapy", Chemical Communications, 2018, vol. 54, pp. 9198-9201.
Mehranpour, A. M. et al., "Synthesis and characterization of new ?-substituted pentamethine cyanine dyes", Synthetic Communications, 2010, vol. 40, pp. 3594-3602.
Yesudas, K. et al., "Cationic cyanine dyes: impact of symmetrybreaking on optical absorption and third-order polarizabilities", Physical Chemistry Chemical Physics, 2013, vol. 15, pp. 19465-19477.
Rada et al., "Experimental Eye Research", 82, 2006, 185-200, p. 190, section 5.

*Primary Examiner* — Shawquia Jackson
(74) *Attorney, Agent, or Firm* — BakerHostetler

(57) ABSTRACT

This current disclosure is directed to charge-transfer heptamethine dyes for NIR singlet oxygen generation, each such dye comprising a near-infrared (NIR) absorbing dye having heptamethine linkages orthogonally coupled to an optionally substituted cationic heteroaryl ring moiety as a charge-transfer partner and uses thereof.

14 Claims, 11 Drawing Sheets
(9 of 11 Drawing Sheet(s) Filed in Color)

IR-780

IR-1061

IR-1061-pyridine

IR-1061-N-methylpyridinium

IR-1061-pyridinium

IR-1061-acridinium

IR-1061-N-methylacridinium

IR-1061-N,N-dimethylaminopyridinium

IR-1061-*p*-nitropyridinium        IR-1061-*p*-dimethylaminopyridinium

NEAR-INFRARED HEPTAMETHINE DYES FOR GENERATION OF SINGLET OXYGEN

CROSS REFERENCE TO RELATED APPLICATIONS

This application claims priority to U.S. Application No. 62/750,095, filed Oct. 24, 2018, the contents of which are incorporated by reference herein for all purposes.

TECHNICAL FIELD

This current disclosure is directed to charge-transfer heptamethine dyes for NIR singlet oxygen generation, each such dye comprising a near-infrared (NIR) absorbing dye having heptamethine linkages orthogonally coupled to a cationic heteroaryl moeities and uses thereof.

BACKGROUND

Singlet oxygen—the first excited state of $O_2$—has significant therapeutic potential. It is already used in a variety of clinical applications, from photodynamic therapy to corneal crosslinking, and new applications continue to emerge. For most therapeutic applications, singlet oxygen is generated in situ via excitation of a photosensitizer. Although this affords unmatched spatiotemporal control over the reactive singlet oxygen molecules, it constrains applications to areas that can be accessed by light. Compared to visible light, NIR light offers several advantages, most notably significantly greater light penetration in the body. Although a number of fluorophores are now being designed with this in mind, there are few small molecule NIR chromophores capable of generating singlet oxygen past 800 nm, and those that can do not absorb significantly above 800 nm. In fact, no single photon chemistry has previously been observed above 900 nm. Different methods—such as two-photon excitation and upconverting nanoparticles—have been proposed to circumvent this issue, but a need remains for small molecules capable of directly generating singlet oxygen using NIR light.

This disclosure is directed to taking advantage of the discoveries cited herein to avoid at least some of the problems associated with previously known methods

SUMMARY

The present disclosure is directed, at least in part, to compositions comprising near-infrared absorbing substrates capable of singlet oxygen sensitization under atmospheric conditions and their uses.

Certain of the embodiments disclosed herein set forth compounds comprising a near-infrared (NIR) absorbing dye having a heptamethine linkage orthogonally coupled to an optionally substituted cationic heteroaryl ring moiety. In independent embodiments, the cationic heteroaryl moiety comprises a cationic nitrogen-containing, an oxygen-containing, or a sulfur-containing heteroaryl ring moiety.

In some aspects, the near-infrared (NIR) absorbing dye within these compounds independently comprises a cyanine structure, a pyrylium structure, or a thiopyrylium structure, or a combination thereof. Various structural permutations and derivatives are more fully set forth below. Such heptamethine dyes (albeit without the substituted cationic heteroaryl moieties) are described in U.S. Pat. Nos. 4,464,383; 5,563,028; 5,633,390; 5,973,158; 6,072,059; 6,515,811; 6,673,943; 9,610,370; and 10,280,307; each of which are incorporated by reference herein at least for its descriptions of the dye portions of the claimed compounds (including backbones and substitution patterns) and for its teachings of the methods of making and using the same.

In some aspects, the near-infrared (NIR) absorbing dye within these compounds independently comprises a cyanine structure.

In some aspects, the compounds comprise a structure of:

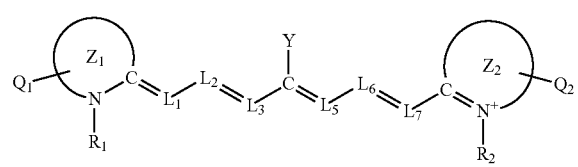

or a rotational or conformational isomer or a salt thereof, wherein $L_1$, $L_2$, $L_3$, $L_5$, $L_6$, and $L_7$ are substituted or unsubstituted methines, wherein the optional substituents are independently $C_{1-6}$ alkyl or $C_{2-6}$ alkenyl; or $L_1$ and $L_3$, or $L_3$ and $L_5$, or $L_5$ and $L_7$ may be linked with a $C_{2-4}$ alkylene or $C_{2-4}$ alkenylene substituent to form a 5- to 7-membered ring;

each of $Z^1$ and $Z^2$ independently comprises a five- or six-membered nitrogen-containing heterocyclic ring, optionally fused to another aryl or heteroaryl ring;

each of $Q_1$ and $Q_2$ is independently H or a substituent positioned on the five- or six-membered nitrogen-containing heterocyclic ring and/or the optionally fused aryl or heteroaryl ring, each optional substituent comprising an optionally substituted $C_{1-12}$ alkyl, $-[CH_2-CH_2-O-]_{1-6}R^{10}$, $C_{2-12}$ alkenyl, polyglycol optionally substituted 5- or 10-membered aryl or heteroaryl group, halo (fluoro, chloro, bromo, iodo), nitro, cyano, $-(C_{0-12}alkyl)$ sulfonate or a salt thereof, $-(C_{0-12}alkyl)$ sulfate or a salt thereof, $-(C_{0-12}alkyl)$phophate or a salt thereof, $-(C_{0-12}alkyl)$hydroxy, $-(C_{0-12}alkyl)$alkoxy, $-(C_{0-12}alkyl)$aryloxy, $-(C_{0-12}alkyl)NHSO_3R_{10}$ or a salt thereof, $-(C_{0-12}alkyl)COOR^{10}$ or a salt thereof, $-(C_{0-12}alkyl)CON(R^{10})_2$, $-(C_{0-12}alkyl)N(R^{10})_2$ or a salt thereof, $-(C_{0-12}alkyl)$borate, $R_1$ and $R_2$ is independently $C_{1-12}$ alkyl, $-[CH_2-CH_2-O-]_{1-6}R^{10}$, $-(C_{0-12}alkyl)$amino acid residue, or a 5- or 6-member ringed aryl or heteroaryl, each of which may be optionally substituted with one or more $-(C_{0-12}alkyl)(SO_3)-R^{10}$ or a salt thereof, $-(C_{0-12}alkyl)(SO_4)-R^{10}$ or a salt thereof, $-(C_{0-12}alkyl)(PO_4)-R^{10}$ or a salt thereof, $-(C_{0-12}alkyl)OR^{10}$, $-(C_{0-12}alkyl)NHSO_3R^{10}$ or a salt thereof, $-(C_{0-12}alkyl)COOR^{10}$ or a salt thereof, $-(C_{0-12}alkyl)CON(R^{10})_2$, $-(C_{0-12}alkyl)N(R^{10})_2$, or $-(C_{0-12}alkyl)$borate or borate ester;

$R^{10}$ is independently H or $C_{1-6}$ alkyl; and

Y is the optionally substituted cationic heteroaryl ring moiety.

Alternatively, or additionally, $Z_1$ and $Z_2$ independently comprise a pyrrole ring, imidazole ring, isothiazole ring, isoxazole ring, oxadiazole ring, oxazole ring, pyrazole ring, pyrimidyl, thiazole ring, selenazole ring, thiadiazole ring, triazole ring, or a pyridine ring, each independently and optionally fused to a phenyl, naphthyl, pyridinyl, quinolinyl, quinoxalinyl, N-alkyl-benzoindolenine, dibenzofuranyl, or dibenzothiophenyl. Other permutation and descriptions for $Z_1$ and $Z_2$, and the other variables are defined elsewhere herein.

Alternatively, or additionally, the near-infrared (NIR) absorbing dye within these compounds independently comprises a pyrylium dye or a thiopyrylium dye structure.

Alternatively, or additionally, in some aspects, the compounds comprise a structure of:

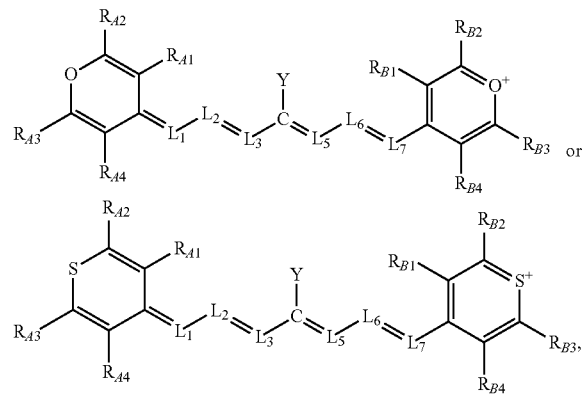

or a rotational or conformational isomer or a salt thereof; wherein $L_1$, $L_2$, $L_3$, $L_5$, $L_6$, and $L_7$ are substituted or unsubstituted methines, wherein the optional substitutents are independently $C_{1-6}$ alkyl or $C_{2-6}$ alkenyl; or $L_1$ and $L_3$, or $L_3$ and $L_5$, or $L_5$ and $L_7$ may be linked with $C_{2-4}$ alkylene or $C_{2-4}$ alkenylene substituents;

$R_{A1}$, $R_{A2}$, $R_{A3}$, $R_{A4}$, $R_{B1}$, $R_{B2}$, $R_{B3}$, and $R_{B4}$ are each independently H, deutrium, or tritium, an $C_{1-12}$ alkyl, —[$CH_2$—$CH_2$—O-]$_{1-6}R^{10}$, $C_{2-12}$ alkenyl, polyglycol optionally substituted 5- or 10-membered aryl or heteroaryl group, halo (fluoro, chloro, bromo, iodo), nitro, cyano, —($C_{0-12}$alkyl) sulfonate or a salt thereof, —($C_{0-12}$alkyl) sulfate or a salt thereof, —($C_{0-12}$alkyl)phophate or a salt thereof, —($C_{0-12}$alkyl)hydroxy, —($C_{0-12}$alkyl)alkoxy, —($C_{0-12}$alkyl)aryloxy, —($C_{0-12}$alkyl)NHSO$_3$R$_{10}$ or a salt thereof, —($C_{0-12}$alkyl)COOR$^{10}$ or a salt thereof, —($C_{0-12}$alkyl)CON(R$^{10}$)$_2$, —($C_{0-12}$alkyl)N(R$^{10}$)$_2$ or a salt thereof, —($C_{0-12}$alkyl)borate;

n is independently 0, 1, 2, 3, or 4, preferably 2;

$R^{10}$ is independently H or $C_{1-6}$ alkyl; and

Y is the optionally substituted cationic heteroaryl ring moiety.

Alternatively, or additionally, in some aspects, the compounds comprise, are substituted with, or are conjugated to at least one isotope of carbon (C-13), fluorine (e.g., F-18), iodine (e.g., I-123, I-125, I-131, I-124), or hydrogen (e.g., tritium, deuterium) enriched above its natural abundance.

The term "orthogonally coupled" refers to a bonding mode in which the orbitals of the heptamethine linkage and optionally substituted cationic heteroaryl ring moiety have limited or no interaction with one another, typically because of steric crowding within the compound. These compounds exhibit significantly improved efficiencies of singlet oxygen generation when irradiated with near-infrared (NIR) light, a process that may be due to formation of a long-lived charge-transfer state that relaxes to an excited triplet state ($T_1$). See, e.g., FIG. 1.

In some independent embodiments, the optionally substituted cationic heteroaryl ring moiety comprises an optionally substituted acridinium, benzoxazolium, benzothiazolium, imidazolium, isoxazolium, isoquinolinium, isothiazolium, naphthoimidazolium, naphthothiazolium, naphthoxazolium, oxazolium, pyrazinium, pyrazolium, pyridimium, pyridinium, quinolinium, tetrazinium, tetrazolium, thiazolium, triazinium, triazolium, benzopyrazinium, benzopyridimium, benzopyridinium, naphthopyrazinium, naphthopyridimium, benzopyridinium, benzotriazinium, naphthotriazinium moiety, pyrylium, chromenylium, xanthylium, thiopyrylium, thiochromenylium, or thioxanthylium moiety. Additional specific embodiments for these moieties are set forth elsewhere herein.

In some independent embodiments, optionally substituted cationic nitrogen-containing heteroaryl or oxygen-containing moiety is bonded to the heptamethine linkage, at any methine carbon, but preferably at the mid-point methine linkage. Typically, the cationic heteroaryl ring moiety is directly bonded to the heptamethine linkage; i.e., no additional linking groups. The optionally substituted cationic nitrogen-containing moiety may be bonded to the linkage by a C—C bond or a C—N bond.

In some independent embodiments, at least one associated cationic group or moiety is internally charged balanced. In other independent embodiments, at least one associated cationic group or moiety is charged balanced by an anionic counter ion, for example a halide anion, e.g. fluoride, chloride, bromide and iodide ions, or other inorganic or organic anion, for example organic anions such as trifluoroacetate, trichloroacetate, triflate, mesylate, and p-toluenesulfonate ions, or inorganic anion such as perchlorate, tetrafluoroborate, hexafluorophosphate, sulfate, hydrogensulfate and nitrate ions. Among the above-exemplified anions, chloride, bromide, perchlorate, tetrafluoroborate, p-toluenesulfonate and trifluoroacetate ions are preferred.

In some independent embodiments, the compound exhibits a local $\lambda_{max}$ for light absorption in a range of from 750 nm to 1400 nm, or any other range set forth elsewhere herein.

In some independent embodiments, the compound generates or is capable of generating singlet oxygen, when the compound is irradiated in the presence of O2 at a wavelength in a range of from 750 nm to 1400 nm, or any other range set forth elsewhere herein.

These compounds, and their ability to generate singlet oxygen when irradiated by NIR light in the presence of oxygen, make them attractive for use in a range of applications. In other aspects, the presence of the optionally substituted cationic heteroaryl ring moiety alters the photophysics of the molecules making them also attractive for use as simple dyes.

For example, and in independent embodiments, these compounds are useful for in vivo imaging, ex vivo imaging (pH sensing and DNA stains), solar energy conversion, or optical filters. Additional uses for these compounds include the treatment and imaging of cancer and other diseases, for example, for use in tumor detection of many cancers with techniques such as magnetic resonance imaging (MRI) and positron emission tomography (PET). For those compounds comprising pendant linking groups (e.g., alkyl carboxylic acid pendants), these pendant groups allow for conjugation to moieties ranging from proteins, cells, tumors, or other biological compositions or moieties to metal surfaces.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present application is further understood when read in conjunction with the appended drawings. For the purpose of illustrating the subject matter, there are shown in the drawings exemplary embodiments of the subject matter; however, the presently disclosed subject matter is not limited to the specific methods, devices, and systems disclosed. In addition, the drawings are not necessarily drawn to scale. In the drawings.

DETAILED DESCRIPTION OF ILLUSTRATIVE EMBODIMENTS

Figure 1:
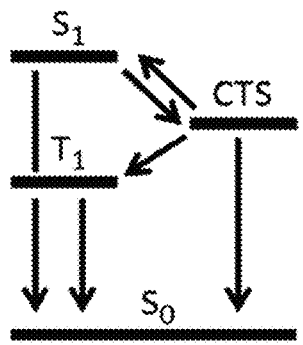
FIG. 1 illustrates a representative Jablonski diagram for orthogonal charge-transfer systems.

The present invention is directed to compounds and compositions comprising these compounds, useful for generating singlet oxygen, when irradiated with near-infrared (NIR) light in the presence of oxygen. These compounds and compositions are also useful for medical and industrial applications set forth herein.

The Compounds

Certain embodiments of the present disclosure comprise compounds comprising a near-infrared (NIR) absorbing dye having a heptamethine linkage coupled to an optionally substituted cationic heteroaryl ring moiety, preferably a cationic heteroaryl ring moiety. In the descriptions throughout, the term "cationic heteroaryl ring moiety" refers to a moiety in which a formal cationic charge resides in and is distributed within the aromatic moiety, and not merely in or on one of the optional substituents of this moiety. Also, the cationic charge may be associated formally with a nitrogen or oxygen or sulfur atom contained within the ring, in which case the heteroaryl ring moiety is referred to as a nitrogen-, oxygen-, or sulfur-containing heteroaryl ring moiety, respectively (and vice versa; i.e., in a nitrogen-, oxygen-, or sulfur-containing heteroaryl ring moiety, the formal cationic charge may be associated with the respective nitrogen, oxygen, or sulfur atoms in the ring structure). Alternatively, or additionally, these moieties may be described as a heteroaryl ring moiety containing an endocyclic nitrogen, oxygen, or sulfur cation. Pyridinium or pyrylium or thiopyrylium are but three non-limiting examples of this principle. Other examples of such moieties are set forth elsewhere herein.

In such structures, the heptamethine linkage is directly bonded to the optionally substituted cationic heteroaryl ring moiety. In those compounds in which the optionally substituted cationic heteroaryl ring moiety is a cationic nitrogen-containing heteroaryl ring moiety, the bonding to the heptamine linkage may be through a C—C bond or a C—N bond (i.e., to a carbon or nitrogen atom of the heteroaryl ring, respectively). In those compounds where the optionally substituted cationic heteroaryl ring moiety is an oxygen- or sulfur-containing heteroaryl ring moiety, the bonding to the heptamine is through a C—C bond with the cationic heteroaryl ring (i.e., to a carbon atom of the heteroaryl ring).

In preferred aspects, the heptamethine linkage is orthogonally coupled to the optionally substituted cationic heteroaryl ring moiety.

As used herein, the term "orthogonally coupled" refers to the state where the n-orbitals of the heptamethine linkage of the dye portion of the compound and the n-orbitals of the optionally substituted cationic heteroaryl ring moiety are orthogonal to one another; i.e., the respective orbitals have limited or no interaction with one another. The spatial relationship between these two sets of orbitals needs not be necessarily perpendicular, as normally associated with the term "orthogonal," so much as the term reflects that there is insufficient overlap as to allow for a pure or effective resonance interaction. Typically, such lack of planarity between the heptamethine linkage and the optionally substituted cationic heteroaryl ring moiety can arise because of steric crowding, owing to the substituents on the dye portion or the cationic heteroaryl portion or both. Such "orthogonal coupling" allows for the provision of a longer-lived charge-transfer state, resulting from a "forbidden" or inefficient ("frustrated") relaxation state.

The portion of the compound set forth as a near-infrared (NIR) absorbing dye having a heptamethine linkage can comprise a cyanine structure, a pyrylium structure, a thiopyrylium structure, or a combination thereof. That is, this dye portion can be envisioned as a moiety having two heteroaryl moieties connected in resonance by a conjugated carbon chain (in this case, a heptamethine linkage, the term "heptamethine linkage" and its numbering scheme being understood by those skilled in the art). The chain contributes to the overall shape of the molecule being linear. The length of the chain determines the wavelength at which the dyes absorb and fluoresce light. Each of these types of structures are considered independent aspects. Examples of each are set forth elsewhere herein.

Cyanine dyes typically consist of two nitrogen-containing heterocycles connected by a conjugated carbon chain. Likewise, pyrylium and thiopyrylium dyes typically each have two pyrylium and thiopyrylium groups, respectively, connected by a conjugated carbon chain. But the present disclosure contemplates all dye structures arising from the various mixed combinations of nitrogen-, oxygen-, and sulfur-containing end groups to the conjugated heptamethine chain. The syntheses of these various dye structures are well understood and documented in the art and need not be elaborated herein. For example, at least U.S. Pat. Nos. 4,283,475; 4,464,383; 5,563,028; 5,633,390; 5,973,158; 6,072,059; 6,515,811; 6,673,943; 9,610,370; and 10,280,307 define structures and syntheses (and uses) or such dyes. Each of these references is incorporated by reference herein at least for its descriptions of dye portion of the claimed compounds (including backbones, substituents, and substitution patterns) and for its teachings of the methods of making and using the same. Further, the modification of these dyes to form the compounds set forth herein, using the methods described at least using the methods disclosed in the Examples, can be readily accomplished by a person of skill in the art, starting from materials disclosed in the foregoing patents.

The present disclosure sets forth compounds, in certain embodiments, comprising a structure of:

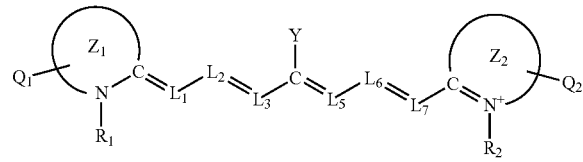

or a rotational or conformational isomer or a salt thereof; wherein $L_1$, $L_2$, $L_3$, $L_5$, $L_6$, and $L_7$ are substituted or unsubstituted methines, wherein the optional substituents are independently $C_{1-6}$ alkyl or $C_{2-6}$ alkenyl; and/or any vicinal pair of methine groups (e.g., $L_1$ and $L_3$, or $L_2$ and $L_4$, or $L_3$ and $L_5$, or $L_4$ and $L_6$, $L_5$ and $L_7$) may be linked with a $C_{2-4}$ alkylene or $C_{2-4}$ alkenylene substituent to form a 5- to 7-membered ring;

each of $Z^1$ and $Z^2$ is independently a five- or six-membered nitrogen-containing heterocyclic ring, optionally fused to another aryl or heteroaryl ring;

each of $Q_1$ and $Q_2$ is independently H or a substituent positioned on the five- or six-membered nitrogen-containing heterocyclic ring and/or the optionally fused aryl or heteroaryl ring, each optional substituent comprising an optionally substituted $C_{1-12}$ alkyl, $-[CH_2-CH_2-O-]_{1-6}R^{10}$, $C_{2-12}$ alkenyl, polyglycol optionally substituted 5- or 10-membered aryl or heteroaryl group, halo (fluoro, chloro, bromo, iodo), nitro, cyano, $-(C_{0-12}alkyl)$ sulfonate or a salt thereof, $-(C_{0-12}alkyl)$ sulfate or a salt thereof, $-(C_{0-12}alkyl)$phophate or a salt thereof, $-(C_{0-12}alkyl)$hydroxy, $-(C_{0-12}alkyl)$alkoxy, $-(C_{0-12}alkyl)$aryloxy, $-(C_{0-12}alkyl)NHSO_3R_{10}$ or a salt thereof, $-(C_{0-12}alkyl)COOR^{10}$ or a salt thereof, $-(C_{0-12}alkyl)CON(R^{10})_2$, $-(C_{0-12}alkyl)N(R^{10})_2$ or a salt thereof, $-(C_{0-12}alkyl)$borate, $R_1$ and $R_2$ is independently $C_{1-12}$ alkyl, $-[CH_2-CH_2-O-]_{1-6}R^{10}$, $-(C_{0-12}alkyl)$amino acid residue, or a 5- or 6-member ringed aryl or heteroaryl, each of which may be optionally substituted with one or more $-(C_{0-12}alkyl)(SO_3)-R^{10}$ or a salt thereof, $-(C_{0-12}alkyl)(SO_4)-R^{10}$ or a salt thereof, $-(C_{0-12}alkyl)(PO_4)-R^{10}$ or a salt thereof, $-(C_{0-12}alkyl)OR^{10}$, $-(C_{0-12}alkyl)NHSO_3R^{10}$ or a salt thereof, $-(C_{0-12}alkyl)COOR^{10}$ or a salt thereof, $-(C_{0-12}alkyl)CON(R^{10})_2$, $-(C_{0-12}alkyl)N(R^{10})_2$, or $-(C_{0-12}alkyl)$borate or borate ester;

$R^{10}$ is independently H or $C_{1-6}$ alkyl; and

Y is the optionally substituted cationic heteroaryl ring moiety.

It should be appreciated that while Y is shown here as being in the $L_4$ position (i.e., between the $L_3$ and $L_5$ methines), and is preferably positioned there, in other aspects, Y can be alternatively positioned on any of the $L_1$, $L_2$, $L_3$, $L_4$, $L_5$, $L_6$, or $L_7$ positions. All geometric and rotational isomers or conformational structures of these illustrated structures (or any of the structures set forth herein) are considered within the scope of this disclosure.

Likewise, it should be appreciated that while $Q_1$, $Q_2$, $R_1$, and $R_2$ are defined in terms of specific optional substituents, and Y is defined merely as "optionally substituted," in some Aspects of this Embodiment, the optional substituents may also include those defined elsewhere herein as Fn. In this regard, any one or more of these Fn substituents is considered to be selected independently, as if listed individually.

$Z_1$ and $Z_2$ may be the same. $Z_1$ and $Z_2$ may be different.

Additionally, or alternatively, the five- or six-membered nitrogen-containing heterocyclic ring of $Z_1$ and $Z_2$ may independently comprise a pyrrole ring, imidazole ring, isothiazole ring, isoxazole ring, oxadiazole ring, oxazole ring, pyrazole ring, pyrimidyl, thiazole ring, selenazole ring, thiadiazole ring, triazole ring, or a pyridine ring.

Additionally, or alternatively, the five- or six-membered nitrogen-containing heterocyclic ring of $Z_1$ and $Z_2$ is independently fused to a phenyl, naphthyl, pyridinyl, quinolinyl, quinoxalinyl, N-alkyl-benzoindolenine, dibenzofuranyl, or dibenzothiophenyl.

Additionally, or alternatively, $Z_1$ and $Z_2$ may independently comprise a benzimidazole ring, benzindole ring, benzoindolenine ring, benzoxazole ring, benzothiazole ring, furopyrrole ring, imidazole ring, imidazoquinoxaline ring, indolenine ring, indolizine ring, isoxazole ring, naphthimidazole ring, naphthothiazole ring, naphthoxazole ring, oxazolocarbazole ring, oxazole ring, oxazolodibenzofuran ring, pyrrolopyridine ring, pyridine ring, quinoline ring, quinoxaline ring, thiazole ring, or naphthoimidazole ring.

Additionally, or alternatively, each of the methines in the $L_1$, $L_2$, $L_3$, $L_4$, $L_5$, $L_6$, or $L_7$ positions not attached to Y may be independently and optionally substituted. In certain aspects, unsubstituted methines may be preferred; i.e., those methines not bonded to Y are otherwise not substituted. For example, where Y is in the $L_4$ position, $L_1=L_2=L_3=L_5=L_6=L_7=CH$. In other aspects, where where Y is in the $L_1$ position, $L_2=L_3=L_4=L_5=L_6=L_7=CH$. In other aspects, where where Y is in the $L_2$ position, $L_1=L_3=L_4=L_5=L_6=L_7=CH$. In other aspects, where where Y is in the $L_3$ position, $L_1=L_2=L_4=L_5=L_6=L_7=CH$.

Additionally, or alternatively, one or more of $L_1$ and $L_3$, or $L_2$ and $L_4$, or $L_3$ and $L_5$, or $L_4$ and $L_6$, $L_5$ and $L_7$ are linked with a $C_{2-4}$ alkylene substituent to form a 5- to 7-membered ring. They may independently be linked with a $C_{2-4}$ alkenylene substituent. The inclusion of such ring structures reinforces the heptamethine backbone, adding structural rigidity to it. Depending in the position of Y in the heptamethine chain, it is possible that two such rings may be included, for example linking $L_1/L_3$ and $L_4/L_7$.

The present disclosure also sets forth compounds, in certain embodiments, comprising a structure of:

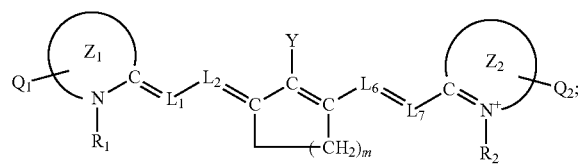

or a rotational or conformational isomer or a salt thereof; where $L_1$, $L_2$, $L_3$, $L_4$, $L_5$, $L_6$, $L_7$, $Q_1$, $R^1$, Y, $Z_1$, are defined in any of the definitions as set forth elsewhere herein in any combination or permutations and m is 1, 2, or 3.

The present disclosure also sets forth compounds, in certain embodiments, comprising a structure of:

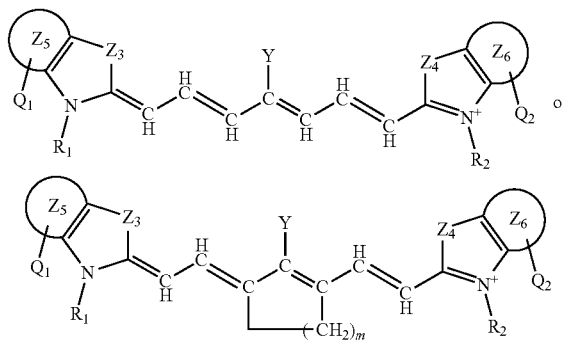

or a rotational or conformational isomer or a salt thereof wherein
each of $Z_3$ and $Z_4$ is independently —$CR^{11}R^{12}$, —O—, —S— or —Se— (each of $Z_3$ and $Z_4$ is independently preferably —$CR^{11}R^{12}$, —O— or —S—, each of $Z_3$ and $Z_4$ is independently more preferably is —$CR^{11}R^{12}$; —O— or —S, each of $Z_3$ and $Z_4$ is independently further preferably is —$CR^{11}R^{12}$ or, and each of $Z_3$ and $Z_4$ is independently most preferably —$CR^{11}R^{12}$);
each of $Z_5$ and $Z_6$ is independently preferably phenyl, naphthyl, pyridinyl, quinolinyl, quinoxalinyl, N-alkyl-benzoindolenine, dibenzofuranyl, or dibenzothiophenyl,
each of $R^{11}$ and $R^{12}$ is independently a $C_{1-6}$ alkyl, preferably methyl; and
$Q_1$ and $Q_2$ are independently, preferably H, —COOH or a salt thereof, or —$SO_3H$ or a salt thereof.

The present disclosure also sets forth compounds, in certain embodiments, comprising a structure of structure:

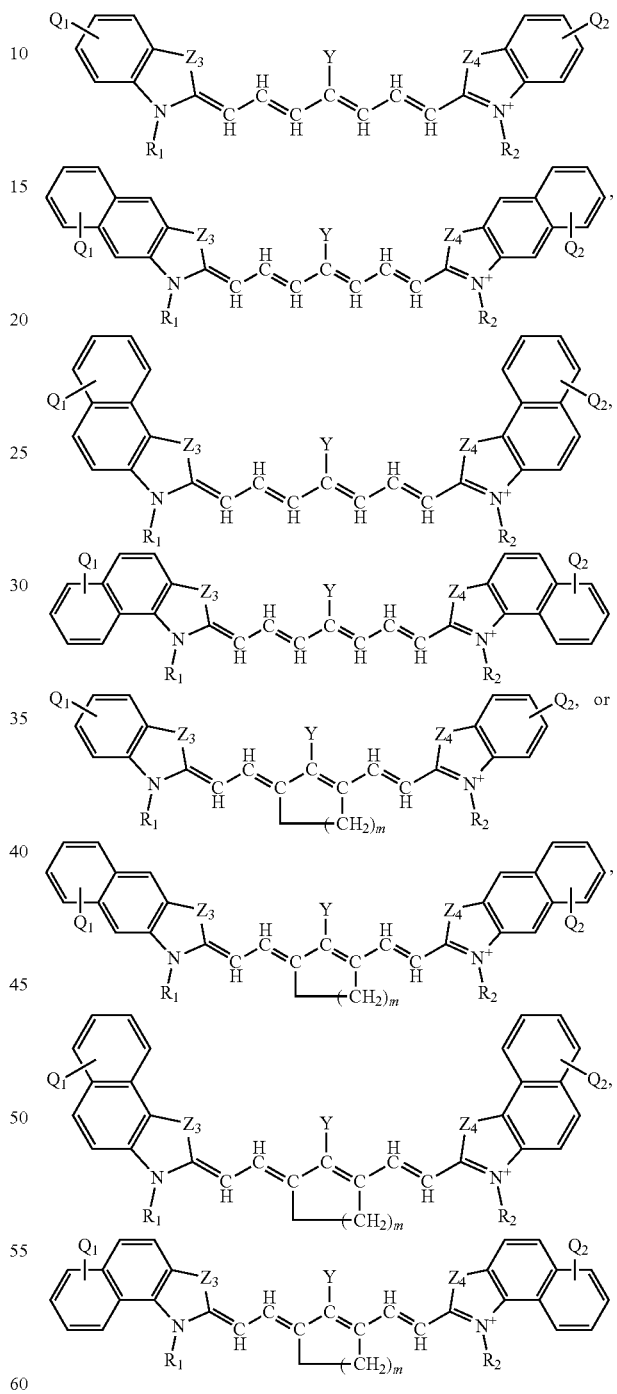

or a rotational or conformational isomer or a salt thereof wherein each of $Z_3$ and $Z_4$ is independently —$CR^{11}R^{12}$, —$NR^{11}$, —O—, —S— or —Se— (each of $Z_3$ and $Z_4$ is independently preferably —$CR^{11}R^{12}$, —$NR^{11}$, —O— or —S—, each of $Z_3$ and $Z_4$ is independently more preferably is —$CR^{11}R^{12}$, —O— or —S, each of $Z_3$ and $Z_4$ is independently further preferably is —CR$^{11}$R$^{12}$ or —O—, and each of Z$_3$ and Z$_4$ is independently most preferably —CR$^{11}$R$^{12}$);

each of R$^{11}$ and R$^{12}$ is independently a C$_{1-6}$ alkyl, preferably methyl;

m=1, 2, or 3; and

Q$_1$ and Q$_2$ are independently, preferably H, —COOH or a salt thereof, or —SO$_3$H or a salt thereof.

Additionally, or alternatively, the fused naphthalene moieties in these preceding structures may be independently replaced with an optionally substituted quinolinyl, quinoxalinyl, N-alkyl-benzoindolenine, dibenzofuranyl, or dibenzothiophenyl ring.

The present disclosure also sets forth compounds, in certain embodiments, comprising a structure of structure:

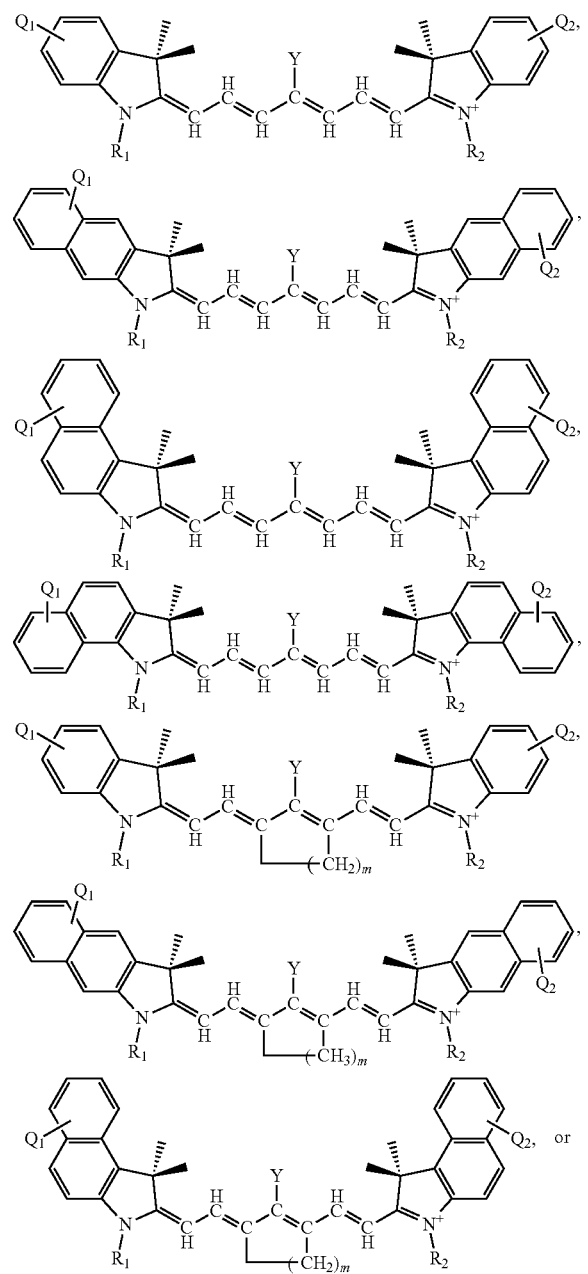

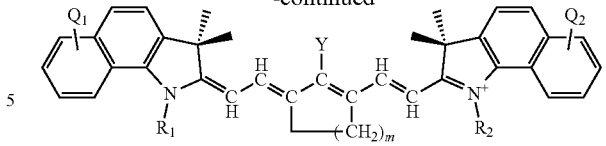

or a rotational or conformational isomer or a salt thereof where R$_1$ and R$^2$ are independently —(C$_{1-12}$alkyl)(SO$_3$)H or a salt thereof or —(C$_{1-12}$alkyl)COOH or a salt thereof. Each of these structures represent independent Aspects of this Embodiment.

Additionally, or alternatively, the fused naphthalene moieties in these preceding structures may be independently replaced with an optionally substituted quinolinyl, quinoxalinyl, N-alkyl-benzoindolenine, dibenzofuranyl, or dibenzothiophenyl ring.

The present disclosure sets forth compounds, in certain embodiments, comprising a structure of:

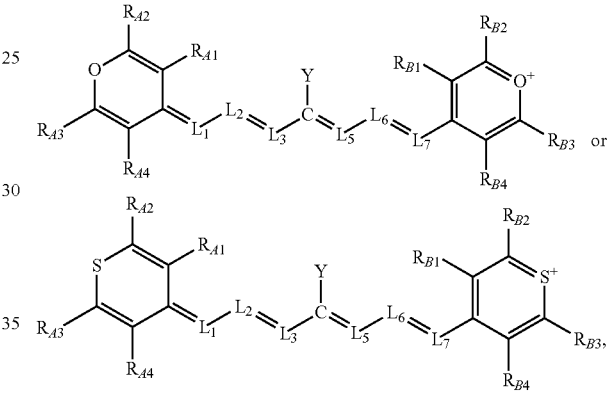

or a rotational or conformational isomer or a salt thereof; wherein

L$_1$, L$_2$, L$_3$, L$_5$, L$_6$, and L$_7$ are substituted or unsubstituted methines, wherein the optional substitutents are independently C$_{1-6}$ alkyl or C$_{2-6}$ alkenyl; or L$_1$ and L$_3$, or L$_3$ and L$_5$, or L$_5$ and L$_7$ may be linked with C$_{2-4}$ alkylene or C$_{2-4}$ alkenylene substituents;

R$_{A1}$, R$_{A2}$, R$_{A3}$, R$_{A4}$, R$_{B1}$, R$_{B2}$, R$_{B3}$, and R$_{B4}$ are each independently H, deutrium, or tritium, an C$_{1-12}$ alkyl, —[CH$_2$—CH$_2$—O-]$_{1-6}$R$^{10}$, C$_{2-12}$ alkenyl, polyglycol optionally substituted 5- or 10-membered aryl or heteroaryl group, halo (fluoro, chloro, bromo, iodo), nitro, cyano, —(C$_{0-12}$alkyl) sulfonate or a salt thereof, —(C$_{0-12}$alkyl) sulfate or a salt thereof, —(C$_{0-12}$alkyl)phophate or a salt thereof, —(C$_{0-12}$alkyl)hydroxy, —(C$_{0-12}$alkyl)alkoxy, —(C$_{0-12}$alkyl)aryloxy, —(C$_{0-12}$alkyl)NHSO$_3$R$_{10}$ or a salt thereof, —(C$_{0-12}$alkyl)COOR$^{10}$ or a salt thereof, —(C$_{0-12}$alkyl)CON(R$^{10}$)$_2$, —(C$_{0-12}$alkyl)N(R$^{10}$)$_2$ or a salt thereof, —(C$_{0-12}$alkyl)borate;

n is independently 0, 1, 2, 3, or 4, preferably 2;

R$^{10}$ is independently H or C$_{1-6}$ alkyl; and

Y is the optionally substituted cationic heteroaryl ring moiety.

It should be appreciated that while Y is shown here as being in the L$_4$ position (i.e., between the L$_3$ and L$_5$ methines), and is preferably positioned there, Y can be alternatively positioned on any of the L$_1$, L$_2$, L$_3$, L$_4$, L$_5$, L$_6$, or L$_7$ positions.

Likewise, it should be appreciated that while Y is defined merely as "optionally substituted," these optional substituents may include those defined elsewhere herein as Fn. Also, $R_{A1}$, $R_{A2}$, $R_{A3}$, $R_{A4}$, $R_{B1}$, $R_{B2}$, $R_{B3}$, and $R_{B4}$ may also independently be any one or more the these Fn substituents.

Additionally, or alternatively, $Z_1$ and $Z_2$ are the same. Additionally, or alternatively, $Z_1$ and $Z_2$ are different.

Additionally, or alternatively, each of the methines in the $L_1$, $L_2$, $L_3$, $L_4$, $L_5$, $L_6$, or $L_7$ positions not attached to Y may be independently and optionally substituted. In certain aspects, unsubstituted methines may be preferred; i.e., those methines not bonded to Y are otherwise not substituted. For example, where Y is in the $L_4$ position, $L_1=L_2=L_3=L_5=L_6=L_7$=CH. In other aspects, where where Y is in the $L_1$ position, $L_2=L_3=L_4=L_5=L_6=L_7$ =CH. In other aspects, where where Y is in the $L_2$ position, $L_1=L_3=L_4=L_5=L_6=L_7$ =CH. In other aspects, where where Y is in the $L_3$ position, $L_1=L_2=L_4=L_5=L_6=L_7$ =CH.

Additionally, or alternatively, one or more of $L_1$ and $L_3$, or $L_2$ and $L_4$, or $L_3$ and $L_5$, or $L_4$ and $L_6$, $L_5$ and $L_7$ are linked with a $C_{2-4}$ alkylene substituent to form a 5- to 7-membered ring. They may independently be linked with a $C_{2-4}$ alkenylene substituent. The inclusion of such ring structures reinforces the heptamethine backbone, adding structural rigidity to it. Depending in the position of Y in the heptamethine chain, it is possible that two such rings may be included, for example linking $L_1/L_3$ and $L_4/L_7$.

The present disclosure sets forth compounds, in certain embodiments, comprising a structure of:

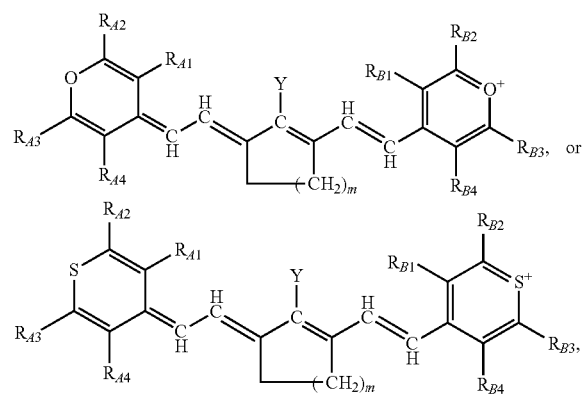

or a rotational or conformational isomer or a salt thereof; where m is 1, 2, or 3.

Additionally, or alternatively, $R_{A1}$, $R_{A4}$, $R_{B1}$, and $R_{B4}$ are H, or an isotope thereof, and $R_{A2}$, $R_{A3}$, $R_{B2}$, and $R_{B3}$ are aryl, heteroaryl, or branched or cyclic alkyl. The terms aryl, heteroaryl, or branched or cyclic alkyl are set forth more broadly elsewhere herein, but in preferred embodiments $R_{A2}$, $R_{A3}$, $R_{B2}$, and $R_{B3}$ are independently phenyl, pyridinyl, or tert-butyl.

As provided throughout, in the compounds, the optionally substituted cationic heteroaryl ring moiety comprises an optionally substituted acridinium, benzoxazolium, benzothiazolium, imidazolium, isoxazolium, isoquinolinium, isothiazolium, naphthoimidazolium, naphthothiazolium, naphthoxazolium, oxazolium, pyrazinium, pyrazolium, pyridimium, pyridinium, quinolinium, tetrazinium, tetrazolium, thiazolium, triazinium, triazolium, benzopyrazinium, benzopyridimium, benzopyridinium, naphthopyrazinium, naphthopyridimium, benzopyridinium, benzotriazinium, naphthotriazinium moiety, pyrylium, chromenylium, xanthylium moiety, thiopyrylium, thiochromenylium, or thioxanthylium moiety. Each of these is to be considered an independent aspect of the embodiments provided herein.

Further, in the context of these optional substituents, these may comprise any one or more of the functional group Fn a set forth elsewhere herein. In this regard, any one or more of these Fn substituents is selected independently, as if listed individually. Further, in the context of these cationic heteroaryl ring moieties, the optional substituents may also comprise fused 5- or 6-membered aryl, heteroaryl, alkyl, or heteroalkyl moieties. Note here that bulky lateral substituents (e.g., ortho- and/or meta- with respect to the point of attachment to the heptamethine linkage) tend to favor steric displacement of the cationic heteroaryl ring moieties away from planarity to the heptamethine linkages, giving rise to the orthogonality of the coupling, though such substituents are not necessarily present.

Additionally, or alternatively, the optionally substituted cationic heteroaryl ring moiety comprises a structure:

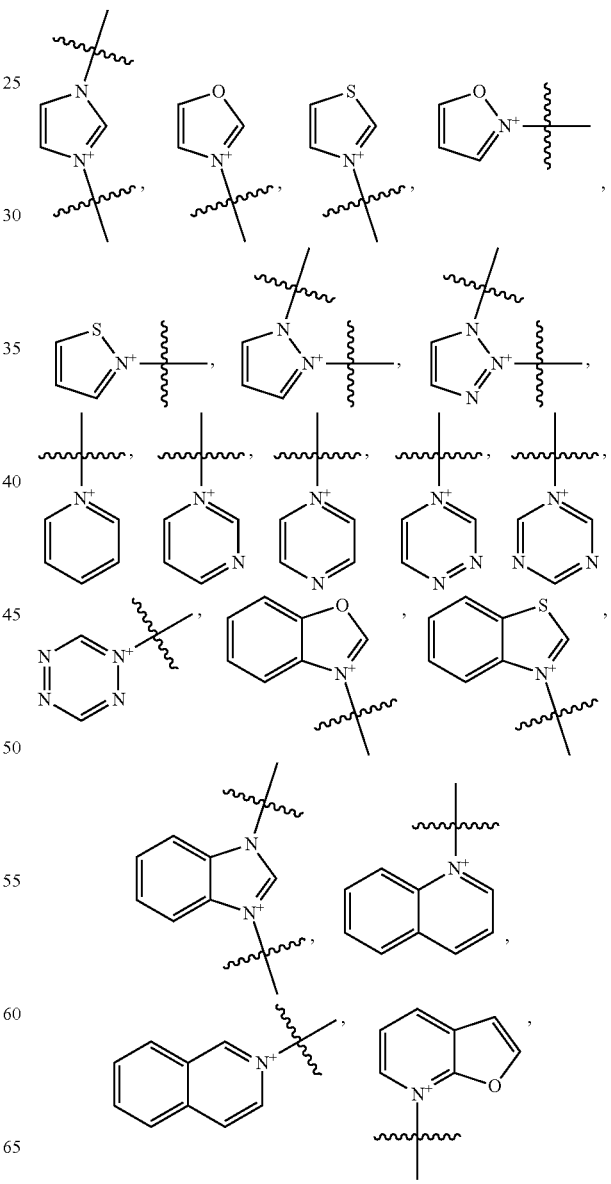

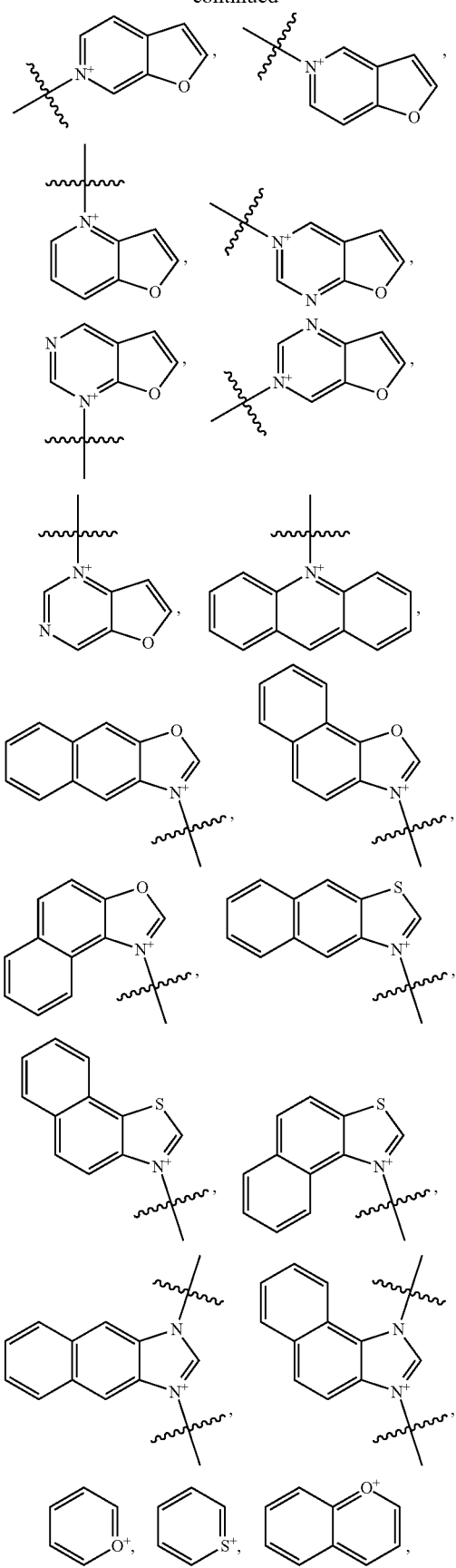

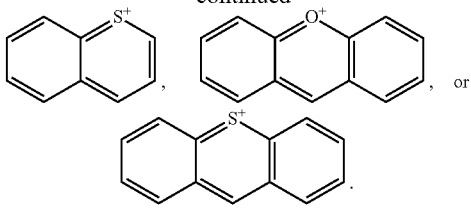

Each of these exemplary structures are considered individual aspects of the embodiments set forth herein, as if individually listed.

The compounds disclosed herein, while containing at least one cationic group in the form of the cationic heteroaryl moieties of Y, may carry a net neutral, net positive, or net negative charge contain depending on the substituents present. For example, the dye portion of the compounds (or even Y) may also have least one of the associated cationic groups or moieties that are internally charged balanced by substituent anionic groups.

Where the compound comprises cationic groups and has a net neutral or net positive charge, wherein at least one of the associated cationic groups or moieties are charge balanced by anionic counter ions. In preferred cases, the anionic counter ions can be halide anions (e.g., fluoride, chloride, bromide, and/or iodide), or other inorganic anions (e.g., perchlorate, tetrafluoroborate, hexafluorophosphate, sulfate, hydrogensulfate and/or nitrate) or organic anions (e.g., organic anions such as trifluoroacetate, trichloroacetate, triflate, mesylate, and/or p-toluenesulfonate ions). Where one or more substituents are anionic (for example, carboxylate or sulfonate anions), they may have associated counter cations, such as alkali metal cations, such as $Li^+$, $Na^+$, or $K^+$. The choice of counter cations or anions should not be limited.

Alternatively, or additionally, in some aspects, the compounds set forth herein may comprises, is substituted with, or is conjugated to at least one isotope of carbon (C-13), fluorine (e.g., F-18), iodine (e.g., 1-123, 1-125, 1-131, 1-124), or hydrogen (e.g., tritium, deuterium) enriched above its natural abundance. Examples of isotopes suitable for inclusion in the compounds described herein include and are not limited to $^2H$, $^3H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. The degree of enrichment can be at least 5 time, at least 10 times, at least 100 time, or at least 1000 times (depending on the nature of the isotope and its natural abundance) above its natural abundance up to completely substituted in that isotope. Isotopically-labeled compounds can be prepared by any suitable method or by processes using an appropriate isotopically-labeled reagent in place of the non-labeled reagent otherwise employed. As such, the compounds may useful for imaging methods, including, but not limited to, use as positron emission tomography (PET) probes, in addition or alternative to their use as simple dyes or singlet oxygen generators. In addition to positron emission tomography (PET), the compounds may be used in single photon emission computed tomography (SPECT), magnetic resonance imaging, (nuclear) magnetic resonance spectroscopy, computed tomography, or a combination thereof.

Alternatively, or additionally, in some aspects, the compounds set forth herein may be conjugated to a biological targeting ligands (e.g., peptides, proteins, antibodies, etc.) through one or more of the substituents associated with the compound.

As set forth elsewhere herein, the disclosed compounds are useful for generating singlet oxygen when irradiated with near-infrared light, but they are also useful as dyes even when irradiated in the absence (or presence) of oxygen. In certain aspects of the embodiments provided herein, the compounds are those that exhibits a local $\lambda_{max}$ for light absorption in a range of from 750 nm to 1400 nm, or at least absorb sufficient light in this range to fulfill its intended purpose. In independent aspects of this feature, this range can be defined in terms of from 750 nm to 800 nm, from 800 nm to 850 nm, from 850 nm to 900 nm, from 900 nm to 950 nm, from 950 nm to 1000 nm, from 1000 nm to 1050 nm, from 1050 nm to 1100 nm, from 1100 nm to 1150 nm, from 1150 nm to 1200 nm, from 1200 nm to 1250 nm, from 1250 to 1300 nm, from 1300 to 1350 nm, from 1350 nm to 1400 nm, or in a range comprising two of more of these foregoing ranges, for example from 800 nm to 1100 nm. Additionally, or alternatively, the compounds are those that can be characterized as generating sufficient singlet oxygen to accommodate the uses set forth elsewhere herein.

Additionally, or alternatively, the compounds are those that generate free radicals, when irradiated in the presence of $O_2$ with light at a wavelength in a range of from 750 nm to 1400 nm. In other independent aspects of this feature, this range can be defined in terms of from 750 nm to 800 nm, from 800 nm to 850 nm, from 850 nm to 900 nm, from 900 nm to 950 nm, from 950 nm to 1000 nm, from 1000 nm to 1050 nm, from 1050 nm to 1100 nm, from 1100 nm to 1150 nm, from 1150 nm to 1200 nm, from 1200 nm to 1250 nm, from 1250 to 1300 nm, from 1300 to 1350 nm, from 1350 nm to 1400 nm, or in a range comprising two of more of these foregoing ranges, for example from 800 nm to 1100 nm.

Additionally, or alternatively, the compounds are those that generates singlet oxygen, when irradiated in the presence of $O_2$ with light at a wavelength in a range of from 750 nm to 1400 nm. In other independent aspects of this feature, this range can be defined in terms of from 750 nm to 800 nm, from 800 nm to 850 nm, from 850 nm to 900 nm, from 900 nm to 950 nm, from 950 nm to 1000 nm, from 1000 nm to 1050 nm, from 1050 nm to 1100 nm, from 1100 nm to 1150 nm, from 1150 nm to 1200 nm, from 1200 nm to 1250 nm, from 1250 to 1300 nm, from 1300 to 1350 nm, from 1350 nm to 1400 nm, or in a range comprising two of more of these foregoing ranges, for example from 800 nm to 1100 nm.

Where reference is made to "in the presence of oxygen," the oxygen may be presented to the compound either as air, air enriched with oxygen, or in other compositions comprising oxygen or in a solvent comprising air, air enriched with oxygen, or in other compositions comprising oxygen (for example, irradiating an oxygenated solution of the compound).

Deuterated Solutions

Additionally, or alternatively, the compounds set forth herein may be present in compositions in which the compound is dissolved or suspended in a solvent, or are in contact with a solvent, wherein the solvent is a partially or fully deuterated solvent or is a solvent comprising a partially or fully deuterated solvent. In certain aspects of this embodiment, the deuterated solvent is or comprises partially or fully deuterated chloroform, dimethyl sulfoxide, methanol, ethanol, tetrahydrofuran, or water or mixtures thereof.

Methods of Use

The compounds set forth herein, and their ability to generate free radicals or singlet oxygen when irradiated by NIR light in the presence of oxygen, make them attractive for use in a range of applications. In other aspects, the presence of the optionally substituted cationic heteroaryl ring moiety alters the photophysics of the molecules making them also attractive for use as simple dyes even in the absence or deficiency of oxygen. That is, the compounds provide the benefits of the ability to absorb near-infrared light, and associated fluorescence, and the ability to generate singlet oxygen, making them useful both as probes and delivery means directed/targeted chemical processes. Such uses include applications ranging from optical filters, display panels, and solar energy conversion through biomedical in vivo imaging, ex vivo imaging (pH sensing and DNA stains), the imaging and treatment of cancer (e.g., tumor detection of many cancers with techniques such as magnetic resonance imaging (MRI) and positron emission tomography (PET). Dyes featuring alkyl carboxylic acids, such as are set forth herein, have been previously explored extensively for both dye-sensitized solar cells and conjugation of other groups onto the dye. The incorporation of such water-soluble acid and sulfonate groups (and their associated pH dependencies and metal binding abilities) allow for these compounds to anchor themselves to metal surface, to chelate metals, and/or to serve as functional links to other targeting biological ligands (e.g., peptides, proteins, antibodies, etc.). The use of these compounds and methods of using these compounds in such ways are within the scope of the present disclosure.

For example, in some aspects, the compounds can be incorporated into one or more optical filters, the optical filter comprising a transparent support (optionally comprising a polymer film) and at least one filter layer, wherein the filter layer contains a compound set forth herein. These optical filters may further be incorporated with into a plasma display panel, such that the plasma display panel comprises a display surface covered with such optical filters, preferably, wherein the optical filter is directly attached to the display surface. Such optical filters and display panels are disclosed, for example, in U.S. Pat. No. 6,515,811, which is incorporated by reference herein for its teachings of such devices. The person of skill in the art would be well equipped to understand the specific features of the compounds disclosed herein that would provide for acceptable or optimal performance. Such appropriate selections are within the scope of the present disclosure.

For example, in some aspects, the compounds can be incorporated into materials suitable for use in photoelectrophoretic photography. Such materials and their applications are set forth, for example, in U.S. Pat. No. 4,283,475, which is incorporated by reference herein for its teachings of the specific attributes of the compounds useful in this application. The person of skill in the art would be well equipped to understand the specific features of the compounds disclosed herein that would provide for acceptable or optimal performance. Such appropriate selections are within the scope of the present disclosure.

For example, in some aspects, the compounds and their use as singlet oxygen generators are useful in methods of crosslinking biological polymers tissues. Such methods comprise contacting a tissue with the compounds or compositions set forth herein and irradiating the compounds or compositions in the presence of oxygen with near-infrared (NIR radiation to generate singlet oxygen, thereby exposing the tissue to the singlet oxygen. Such methods are set forth, at least in part, in a co-filed, co-pending application, client reference number 103693.000495/CIT-8183, titled "TREATMENT OF MYOPIA AND OTHER OCULAR CONDITIONS USING SINGLET OXYGEN GENER- ATED FROM DYES ACTIVATED BY NEAR-INFRARED LIGHT," which is incorporated by reference herein in its entirety for all purposes, or at least for its teaching of the methods and materials useful for such tissue restructuring.

For example, in some aspects, the compounds and their optional use as singlet oxygen generators are useful in imaging and treating cells, including tumor cells, including cancer cells and tumors, especially when the compounds are functionalized for attachment to such tissues, cells, and/or tumors. In certain aspects of these embodiments, the methods comprise imaging a bio-substrate or a living cell, the methods comprising interacting one or more of the compounds set forth herein with the biosubstrate or the living cell; and observing said biosubstrate or living cell, either by naked eye or through use of a specialized instrument. Such specialized instrument may be, for example, a confocal laser scanning microscope. In certain aspects of these embodiments, the bio-substrate is a DNA, a protein, or a liposome. In other aspects of these embodiments, the imaging can be done in vivo. In still other aspects of these embodiments, the imaging is done ex vivo. Such methods are set forth in U.S. Pat. No. 8,735,601, which is incorporated by reference herein for its teachings of such methods. The person of skill in the art would be well equipped to understand the specific features of the compounds disclosed herein that would provide for acceptable or optimal performance. Such appropriate selections are within the scope of the present disclosure.

For example, in some aspects, the compounds may be used in methods for detecting fluid viscosity, each method comprising: (1) introducing a compound as set forth herein into an intracellular fluid; (2) measuring a fluorescence intensity or a fluorescence life time of the fluid obtained in step (1): (3) correlating a change in the fluorescence intensity or the fluorescence lifetime to a change in the fluid viscosity. Such methods are set forth in U.S. Pat. No. 8,889,887, which is incorporated by reference herein for its teachings of such methods. The person of skill in the art would be well equipped to understand the specific features of the compounds disclosed herein that would provide for acceptable or optimal performance. Such appropriate selections are within the scope of the present disclosure.

For example, in some aspects, the compounds comprise a moiety capable of binding to cells in a solution and can be used in a method comprising performing flow cytometry to separate cells to which the compound has bound from cells to which the compound did not bind.

For example, in some aspects, the compounds and their optional use as singlet oxygen generators are useful in methods comprising contacting a biological sample or a biosubstrate with such a compound set forth herein and irradiating the biological sample or biosubstrate by application of light having a wavelength or range of wavelengths in the near-infrared range. Alternatively, or additionally, in some aspects, the biological sample is a bodily fluid or tissue. Such methods may further comprise observing the resulting fluorescence either by naked eye or through use of a specialized instrument, as set forth above.

In certain aspects of these embodiments, the method may further comprise detecting fluorescence of the irradiated biological sample, wherein fluorescence indicates presence of the compound in the biological sample.

In certain aspects of these embodiments, the compound comprise a biomolecule capable of binding to a target present or suspected of being present within the biological sample or biosubstrate and fluorescence indicates the target is present in the biological sample. In further aspects, the method may further comprise removing unbound compound from the biological sample prior to obtaining the image.

In certain aspects of these embodiments, the method comprises irradiating the biological sample which comprises irradiating a target area of the subject with near-infrared radiation; and detecting fluorescence comprises obtaining an image of the irradiated target area, wherein fluorescence in the image indicates presence of the target in the target area.

In still further aspects of these embodiments, the target is a tumor and the target area is an area in which the tumor is located. In certain aspects of these embodiments, the method further comprising excising fluorescent tumor cells from the target area.

In certain aspects of these embodiments, the target comprises cancer cells, optionally less than tumor-sized, the method further comprises, irradiating the compound with near-infrared radiation in the presence of oxygen, such that the irradiating generates singlet oxygen known to be detrimental to cancer cells. And the method results in the destruction or inactivation of the cancer cells.

Where described as such, the detecting of fluorescence may comprise obtaining a fluorescence-based image of the irradiated biological sample.

In certain aspects of these embodiments, the compound set forth herein comprises a biomolecule (targeting ligand) capable of binding to a target suspected of being present within the biological sample and fluorescence indicates the target is present in the biological sample, the method further comprising: removing unbound compound from the biological sample prior to obtaining the image. In certain of these aspects, the target is an antigen, and the compound is conjugated to an antibody capable of recognizing and binding to the antigen.

Such methods in these embodiments are set forth in U.S. Pat. Nos. 9,610,370 and 10,280,307, which are incorporated by reference herein for their teachings of such methods. The person of skill in the art would be well equipped to understand the specific features of the compounds disclosed herein that would provide for acceptable or optimal performance. Such appropriate selections are within the scope of the present disclosure.

Terms

The present invention may be understood more readily by reference to the following description taken in connection with the accompanying Figures and Examples, all of which form a part of this disclosure. It is to be understood that this invention is not limited to the specific products, methods, conditions or parameters described or shown herein, and that the terminology used herein is for describing particular embodiments by way of example only and is not intended to be limiting of any claimed invention. Similarly, unless specifically otherwise stated, any description as to a possible mechanism or mode of action or reason for improvement is meant to be illustrative only, and the invention herein is not to be constrained by the correctness or incorrectness of any such suggested mechanism or mode of action or reason for improvement. Throughout this text, it is recognized that the descriptions refer to compositions and methods of making and using said compositions. That is, where the disclosure describes or claims a feature or embodiment associated with a composition or a method of making or using a composition, it is appreciated that such a description or claim is intended to extend these features or embodiment to embodiments in each of these contexts (i.e., compositions, methods of making, and methods of using).

In the present disclosure the singular forms "a," "an," and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When a value is expressed as an approximation by use of the descriptor "about," it will be understood that the particular value forms another embodiment. In general, use of the term "about" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about." In other cases, the gradations used in a series of values may be used to determine the intended range available to the term "about" for each value. Where present, all ranges are inclusive and combinable. That is, references to values stated in ranges include every value within that range.

It is to be appreciated that certain features of the invention which are, for clarity, described herein in the context of separate embodiments, may also be provided in combination in a single embodiment. That is, unless obviously incompatible or specifically excluded, each individual embodiment is deemed to be combinable with any other embodiment(s) and such a combination is considered to be another embodiment. Conversely, various features of the invention that are, for brevity, described in the context of a single embodiment, may also be provided separately or in any sub-combination. Finally, while an embodiment may be described as part of a series of steps or part of a more general structure, each said step may also be considered an independent embodiment in itself, combinable with others.

The transitional terms "comprising," "consisting essentially of," and "consisting" are intended to connote their generally in accepted meanings in the patent vernacular; that is, (i) "comprising," which is synonymous with "including," "containing," or "characterized by," is inclusive or open-ended and does not exclude additional, unrecited elements or method steps; (ii) "consisting of" excludes any element, step, or ingredient not specified in the claim; and (iii) "consisting essentially of" limits the scope of a claim to the specified materials or steps "and those that do not materially affect the basic and novel characteristic(s)" of the claimed invention. In cases here, the the basic and novel characteristic(s) of the compositions here are the ability to generate singlet oxygen when irradiated with near-infrared radiation in the presence of oxygen. Embodiments described in terms of the phrase "comprising" (or its equivalents), also provide, as embodiments, those which are independently described in terms of "consisting of" and "consisting essentially of"

When a list is presented, unless stated otherwise, it is to be understood that each individual element of that list, and every combination of that list, is a separate embodiment. For example, a list of embodiments presented as "A, B, or C" is to be interpreted as including the embodiments, "A," "B," "C," "A or B," "A or C," "B or C," or "A, B, or C." Similarly, a designation such as $C_{1-3}$ includes $C_1$, $C_2$, $C_3$, $C_{1-2}$, $C_{2-3}$, $C_{1,3}$, as separate embodiments, as well as $C_{1-3}$.

Throughout this specification, words are to be afforded their normal meaning, as would be understood by those skilled in the relevant art. However, so as to avoid misunderstanding, the meanings of certain terms will be specifically defined or clarified.

The term "alkyl" as used herein refers to a linear, branched, or cyclic saturated hydrocarbon group typically although not necessarily containing 1 to about 24 carbon atoms, preferably 1 to about 12 carbon atoms, such as methyl, ethyl, n-propyl, isopropyl, n-butyl, isobutyl, tert-butyl, octyl, decyl, and the like, as well as cycloalkyl groups such as cyclopentyl, cyclohexyl and the like. Generally, although again not necessarily, alkyl groups herein contain 1 to about 12 carbon atoms. The term "lower alkyl" intends an alkyl group of 1 to 6 carbon atoms, and the specific term "cycloalkyl" intends a cyclic alkyl group, typically having 4 to 8, preferably 5 to 7, carbon atoms. The term "substituted alkyl" refers to alkyl groups substituted with one or more substituent groups, and the terms "heteroatom-containing alkyl" and "heteroalkyl" refer to alkyl groups in which at least one carbon atom is replaced with a heteroatom. If not otherwise indicated, the terms "alkyl" and "lower alkyl" include linear, branched, cyclic, unsubstituted, substituted, and/or heteroatom-containing alkyl and lower alkyl groups, respectively.

The term "alkylene" as used herein refers to a difunctional linear, branched, or cyclic alkyl group, where "alkyl" is as defined above.

The term "alkenyl" as used herein refers to a linear, branched, or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Preferred alkenyl groups herein contain 2 to about 12 carbon atoms. The term "lower alkenyl" intends an alkenyl group of 2 to 6 carbon atoms, and the specific term "cycloalkenyl" intends a cyclic alkenyl group, preferably having 5 to 8 carbon atoms. The term "substituted alkenyl" refers to alkenyl groups substituted with one or more substituent groups, and the terms "heteroatom-containing alkenyl" and "heteroalkenyl" refer to alkenyl groups in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl groups, respectively.

The term "alkenylene" as used herein refers to a difunctional linear, branched, or cyclic alkenyl group, where "alkenyl" is as defined above.

The term "alkynyl" as used herein refers to a linear or branched hydrocarbon group of 2 to about 24 carbon atoms containing at least one triple bond, such as ethynyl, n-propynyl, and the like. Preferred alkynyl groups herein contain 2 to about 12 carbon atoms. The term "lower alkynyl" intends an alkynyl group of 2 to 6 carbon atoms. The term "substituted alkynyl" refers to an alkynyl group substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include a linear, branched, unsubstituted, substituted, and/or heteroatom-containing alkynyl and lower alkynyl group, respectively.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms. Analogously, "alkenyloxy" and "lower alkenyloxy" respectively refer to an alkenyl and lower alkenyl group bound through a single, terminal ether linkage, and "alkynyloxy" and "lower alkynyloxy" respectively refer to an alkynyl and lower alkynyl group bound through a single, terminal ether linkage.

The term "aromatic" refers to the ring moieties which satisfy the Hückel 4n+2 rule for aromaticity, and includes both aryl (i.e., carbocyclic) and heteroaryl (also called heteroaromatic) structures, including aryl, aralkyl, alkaryl, heteroaryl, heteroaralkyl, or alk-heteroaryl moieties, or prepolymeric (e.g., monomeric, dimeric), oligomeric or polymeric analogs thereof. While the descriptions of the methods and systems involving KOH are provided in terms of heteroaromatic substrates, where their operability is preferred, it is reasonably believed that they also work on aryl substrates.

The term "aryl" as used herein, and unless otherwise specified, refers to an aromatic substituent or structure containing a single aromatic ring or multiple aromatic rings that are fused together, directly linked, or indirectly linked (such that the different aromatic rings are bound to a common group such as a methylene or ethylene moiety). Unless otherwise modified, the term "aryl" refers to carbocyclic structures. Preferred aryl groups contain 5 to 24 carbon atoms, and particularly preferred aryl groups contain 5 to 14 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituents in which at least one carbon atom is replaced with a heteroatom, as will be described in further detail infra.

The term "aryloxy" as used herein refers to an aryl group bound through a single, terminal ether linkage, wherein "aryl" is as defined above. An "aryloxy" group may be represented as —O-aryl where aryl is as defined above. Preferred aryloxy groups contain 5 to 24 carbon atoms, and particularly preferred aryloxy groups contain 5 to 14 carbon atoms. Examples of aryloxy groups include, without limitation, phenoxy, o-halo-phenoxy, m-halo-phenoxy, p-halo-phenoxy, o-methoxy-phenoxy, m-methoxy-phenoxy, p-methoxy-phenoxy, 2,4-dimethoxy-phenoxy, 3,4,5-trimethoxy-phenoxy, and the like.

The term "alkaryl" refers to an aryl group with an alkyl substituent, and the term "aralkyl" refers to an alkyl group with an aryl substituent, wherein "aryl" and "alkyl" are as defined above. Preferred alkaryl and aralkyl groups contain 6 to 24 carbon atoms, and particularly preferred alkaryl and aralkyl groups contain 6 to 16 carbon atoms. Alkaryl groups include, for example, p-methylphenyl, 2,4-dimethylphenyl, p-cyclohexylphenyl, 2,7-dimethylnaphthyl, 7-cyclooctylnaphthyl, 3-ethyl-cyclopenta-1,4-diene, and the like. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. The terms "alkaryloxy" and "aralkyloxy" refer to substituents of the formula —OR wherein R is alkaryl or aralkyl, respectively, as just defined.

The term "acyl" refers to substituents having the formula —(CO)-alkyl, —(CO)-aryl, or —(CO)-aralkyl, and the term "acyloxy" refers to substituents having the formula —O(CO)-alkyl, —O(CO)-aryl, or —O(CO)-aralkyl, wherein "alkyl," "aryl, and "aralkyl" are as defined above.

The terms "cyclic" and "ring" refer to alicyclic or aromatic groups that may or may not be substituted and/or heteroatom-containing, and that may be monocyclic, bicyclic, or polycyclic. The term "alicyclic" is used in the conventional sense to refer to an aliphatic cyclic moiety, as opposed to an aromatic cyclic moiety, and may be monocyclic, bicyclic, or polycyclic. The term "acyclic" refers to a structure in which the double bond is not contained within a ring structure.

The terms "halo," "halide," and "halogen" are used in the conventional sense to refer to a chloro, bromo, fluoro, or iodo substituent.

The term "heteroatom-containing" as in a "heteroatom-containing hydrocarbyl group" refers to a hydrocarbon molecule or a hydrocarbyl molecular fragment in which one or more carbon atoms is replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and heteroaromatic" respectively refer to "aryl" and "aromatic" substituents that are heteroatom-containing, and the like. It should be noted that a "heterocyclic" group or compound may or may not be aromatic, and further that "heterocycles" may be monocyclic, bicyclic, or polycyclic as described above with respect to the term "aryl." Examples of heteroalkyl groups include alkoxyaryl, alkylsulfanyl-substituted alkyl, N-alkylated amino alkyl, and the like. Non-limiting heteroaryl moieties include those an optionally substituted furan, pyrrole, thiophene, pyrazole, imidazole, triazole, isoxazole, oxazole, thiazole, isothiazole, oxadiazole, pyridine, pyridazine, pyrimidine, pyrazine, triazone, benzofuran, benzopyrrole, benzothiophene, isobenzofuran, isobenzopyrrole, isobenzothiophene, indole, isoindole, indolizine, indazole, azaindole, benzisoxazole, benzoxazole, quinoline, isoquinoline, cinnoline, quinazoline, naphthyridine, 2,3-dihydrobenzofuran, 2,3-dihydrobenzopyrrole, 2,3-dihydrobenzothiophene, dibenzofuran, xanthene, dibenzopyrol, dibenzothiophene. In more preferred embodiments, the substrate comprises a moiety comprising an optionally substituted furan, pyrrole, thiophene, pyrazole, imidazole, benzofuran, benzopyrrole, benzothiophene, indole, azaindole dibenzofuran, xanthene, dibenzopyrrole, or dibenzothiophene moiety.

Non-limiting examples of nitrogen-containin heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups are pyrrolidino, morpholino, piperazino, piperidino, etc.

As used herein, the term "moiety" refers to a part of a molecule which is typically given a name as it can be found within other kinds of molecules as well. In some instances, moieties may be composed of yet smaller moieties and functional groups. For example, a As used herein, the terms "substrate" or "organic substrate" are intended to connote both discrete small molecules (sometimes described as "organic compounds") and oligomers and polymers containing such "aromatic moieties." The term "aromatic moieties" is intended to refer to those portions of the compounds, pre-polymers (i.e., monomeric compounds capable of polymerizing), oligomers, or polymers having at least one of the indicated aromatic structure. Where shown as structures, the moieties contain at least that which is shown, as well as containing further functionalization, substituents, or both, including but not limited to the functionalization described as "Fn" herein.

By "substituted" as in "substituted hydrocarbyl," "substituted alkyl," "substituted aryl," and the like, as alluded to in some of the aforementioned definitions, is meant that in the hydrocarbyl, alkyl, aryl, heteroaryl, or other moiety, at least one hydrogen atom bound to a carbon (or other) atom is replaced with one or more non-hydrogen substituents. Examples of such substituents include, without limitation: functional groups referred to herein as "Fn," such as halo (e.g., F, Cl, Br, I), hydroxyl, sulfhydryl, $C_1$-$C_{24}$ alkoxy, $C_2$-$C_{24}$ alkenyloxy, $C_2$-$C_{24}$ alkynyloxy, $C_5$-$C_{24}$ aryloxy, $C_6$-$C_{24}$ aralkyloxy, $C_6$-$C_{24}$ alkaryloxy, acyl (including $C_1$-$C_{24}$ alkylcarbonyl (—CO-alkyl) and $C_6$-$C_{24}$ arylcarbonyl (—CO-aryl)), acyloxy (—O-acyl, including $C_2$-$C_{24}$ alkylcarbonyloxy (—O—CO-alkyl) and $C_6$-$C_{24}$ arylcarbonyloxy (—O—CO-aryl)), $C_2$-$C_{24}$ alkoxycarbonyl ((CO)—O-alkyl), $C_6$-$C_{24}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{24}$ arylcarbonato (—O—(CO)—O-aryl), carboxy (—COOH), carboxylato (—COO—), carbamoyl (—(CO)—NH$_2$), mono-($C_1$-$C_{24}$ alkyl)-substituted carbamoyl (—(CO)NH($C_1$-$C_{24}$ alkyl)), di-($C_1$-$C_{24}$ alkyl)-substituted carbamoyl (—(CO)—N($C_1$-$C_{24}$ alkyl)$_2$), mono-($C_1$-$C_{24}$ haloalkyl)-substituted carbamoyl (—(CO)—NH($C_1$-$C_{24}$ alkyl)), di-($C_1$-$C_{24}$ haloalkyl)-substituted carbamoyl (—(CO)—N($C_1$-$C_{24}$ alkyl)$_2$), mono-($C_5$-$C_{24}$ aryl)-substituted carbamoyl (—(CO)—NH-aryl), di-($C_5$-$C_{24}$ aryl)-substituted carbamoyl (—(CO)—N($C_5$-$C_{24}$ aryl)$_2$), di-N—($C_1$-$C_{24}$ alkyl), N—($C_5$-$C_{24}$ aryl)-substituted carbamoyl, thiocarbamoyl (—(CS)—NH$_2$), mono-($C_1$-$C_{24}$ alkyl)-substituted thiocarbamoyl (—(CO)—NH($C_1$-$C_{24}$ alkyl)), di-($C_1$-$C_{24}$ alkyl)-substituted thiocarbamoyl (—(CO)—N($C_1$-$C_{24}$ alkyl)$_2$), mono-($C_5$-$C_{24}$ aryl)-substituted thiocarbamoyl (—(CO)—NH-aryl), di-($C_5$-$C_{24}$ aryl)-substituted thiocarbamoyl (—(CO)—N($C_5$-$C_{24}$ aryl)$_2$), di-N—($C_1$-$C_{24}$ alkyl), N—($C_5$-$C_{24}$ aryl)-substituted thiocarbamoyl, carbamido (—NH—(CO)—NH$_2$), cyano(~C≡N), cyanato (—O—C≡N), thiocyanato (—S—C≡N), formyl (—(CO)—H), thioformyl (—(CS)—H), amino (—NH$_2$), mono-($C_1$-$C_{24}$ alkyl)-substituted amino, di-($C_1$-$C_{24}$ alkyl)-substituted amino, mono-($C_5$-$C_{24}$ aryl)-substituted amino, di-($C_5$-$C_{24}$ aryl)-substituted amino, $C_1$-$C_{24}$ alkylamido (—NH—(CO)-alkyl), $C_6$-$C_{24}$ arylamido (—NH—(CO)-aryl), imino (—CR=NH where R=hydrogen, $C_1$-$C_{24}$ alkyl, $C_5$-$C_{24}$ aryl, $C_6$-$C_{24}$ alkaryl, $C_6$-$C_{24}$ aralkyl, etc.), $C_2$-$C_{20}$ alkylimino (—CR=N(alkyl), where R=hydrogen, $C_1$-$C_{24}$ alkyl, $C_5$-$C_{24}$ aryl, $C_6$-$C_{24}$ alkaryl, $C_6$-$C_{24}$ aralkyl, etc.), arylimino (—CR=N(aryl), where R=hydrogen, $C_1$-$C_{20}$ alkyl, $C_5$-$C_{24}$ aryl, $C_6$-$C_{24}$ alkaryl, $C_6$-$C_{24}$ aralkyl, etc.), nitro (—NO$_2$), nitroso (—NO), sulfo (—SO$_2$OH), sulfonate (SO$_2$O—), $C_1$-$C_{24}$ alkylsulfanyl (—S-alkyl; also termed "alkylthio"), $C_5$-$C_{24}$ arylsulfanyl (—S-aryl; also termed "arylthio"), $C_1$-$C_{24}$ alkylsulfinyl (—(SO)-alkyl), $C_5$-$C_{24}$ arylsulfinyl (—(SO)-aryl), $C_1$-$C_{24}$ alkylsulfonyl (—SO$_2$-alkyl), $C_1$-$C_{24}$ monoalkylaminosulfonyl-SO$_2$—N(H) alkyl), $C_1$-$C_{24}$ dialkylaminosulfonyl-SO$_2$—N(alkyl), $C_5$-$C_{24}$ arylsulfonyl (—SO$_2$-aryl), boryl (—BH$_2$), borono (—B(OH)$_2$), boronato (—B(OR)$_2$ where R is alkyl or other hydrocarbyl), phosphono (—P(O)(OH)$_2$), phosphonato (—P(O)(O)$_2$), phosphinato (P(O)(O—)), phospho (—PO$_2$), and phosphine (—PH$_2$); and the hydrocarbyl moieties $C_1$-$C_{24}$ alkyl (preferably $C_1$-$C_{12}$ alkyl, more preferably $C_1$-$C_6$ alkyl), $C_2$-$C_{24}$ alkenyl (preferably $C_2$-$C_{12}$ alkenyl, more preferably $C_2$-$C_6$ alkenyl), $C_2$-$C_{24}$ alkynyl (preferably $C_2$-$C_{12}$ alkynyl, more preferably $C_2$-$C_6$ alkynyl), $C_5$-$C_{24}$ aryl (preferably $C_5$-$C_{24}$ aryl), $C_6$-$C_{24}$ alkaryl (preferably $C_6$-$C_{16}$ alkaryl), and $C_6$-$C_{24}$ aralkyl (preferably $C_6$-$C_{16}$ aralkyl). Within these substituent structures, the "alkyl," "alkylene," "alkenyl," "alkenylene," "alkynyl," "alkynylene," "alkoxy," "aromatic," "aryl," "aryloxy," "alkaryl," and "aralkyl" moieties may be optionally fluorinated or perfluorinated. Additionally, reference to alcohols, aldehydes, amines, carboxylic acids, ketones, or other similarly reactive functional groups also includes their protected analogs. For example, reference to hydroxy or alcohol also includes those substituents wherein the hydroxy is protected by acetyl (Ac), benzoyl (Bz), benzyl (Bn, Bnl), β-Methoxyethoxymethyl ether (MEM), dimethoxytrityl, [bis-(4-methoxyphenyl)phenylmethyl] (DMT), methoxymethyl ether (MOM), methoxytrityl [(4-methoxyphenyl)diphenylmethyl, MMT), p-methoxybenzyl ether (PMB), methylthiomethyl ether, pivaloyl (Piv), tetrahydropyranyl (THP), tetrahydrofuran (THF), trityl (triphenylmethyl, Tr), silyl ether (most popular ones include trimethylsilyl (TMS), tert-butyldimethylsilyl (TBDMS), tri-iso-propylsilyloxymethyl (TOM), and triisopropylsilyl (TIPS) ethers), ethoxyethyl ethers (EE). Reference to amines also includes those substituents wherein the amine is protected by a BOC glycine, carbobenzyloxy (Cbz), p-methoxybenzyl carbonyl (Moz or MeOZ), tert-butyloxycarbonyl (BOC), 9-fluorenylmethyloxycarbonyl (FMOC), acetyl (Ac), benzoyl (Bz), benzyl (Bn), carbamate, p-methoxybenzyl (PMB), 3,4-dimethoxybenzyl (DMPM), p-methoxyphenyl (PMP), tosyl (Ts) group, or sulfonamide (Nosyl & Nps) group. Reference to substituent containing a carbonyl group also includes those substituents wherein the carbonyl is protected by an acetal or ketal, acylal, or diathane group. Reference to substituent containing a carboxylic acid or carboxylate group also includes those substituents wherein the carboxylic acid or carboxylate group is protected by its methyl ester, benzyl ester, tert-butyl ester, an ester of 2,6-disubstituted phenol (e.g. 2,6-dimethylphenol, 2,6-diisopropylphenol, 2,6-di-tert-butylphenol), a silyl ester, an orthoester, or an oxazoline. Preferred substituents are those identified herein as not or less affecting the silylation chemistries, for example, including those substituents comprising alkyls; alkoxides, aryloxides, aralkylalkoxides, protected carbonyl groups; aryls optionally substituted with F, Cl, —CF$_3$; epoxides; N-alkyl aziridines; cis- and trans-olefins; acetylenes; pyridines, primary, secondary and tertiary amines; phosphines; and hydroxides.

By "functionalized" as in "functionalized hydrocarbyl," "functionalized alkyl," "functionalized olefin," "functionalized cyclic olefin," and the like, is meant that in the hydrocarbyl, alkyl, aryl, heteroaryl, olefin, cyclic olefin, or other moiety, at least one hydrogen atom bound to a carbon (or other) atom is replaced with one or more functional groups such as those described herein and above. The term "functional group" is meant to include any functional species that is suitable for the uses described herein. In particular, as used herein, a functional group would necessarily possess the ability to react with or bond to corresponding functional groups on a substrate surface.

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

The term "targeting ligand" as used in the present disclosure indicates any molecule that can is conjugated to the compounds set forth herein for the purpose of engaging a specific target, and in particular specific cellular recognition. Examples of suitable ligands include, but are not limited to, vitamins (e.g. folic acid), proteins (e.g. transferrin, monoclonal antibodies), monosaccharides, peptides, and polysaccharides. The term "protein" as used herein indicates a polypeptide with a particular secondary and tertiary structure that can participate in, but not limited to, interactions with other biomolecules including other proteins, DNA, RNA, lipids, metabolites, hormones, chemokines, and small molecules. Exemplary proteins herein described are antibodies. The term protein embraces fusion proteins.

The term "UV-Visible light" as used herein refers to electromagnetic radiation having a wavelength in a range of from about 200 nm to about 750 nm. Individual embodiments describing UV-Visible light as an important parameter include those in which the range of wavelengths include one or more ranges encompassing 200 to 250 nm, 250 to 300 nm, 300 to 350 nm, 350 to 400 nm, 400 to 450 nm, 450 to 500 nm, 500 to 550 nm, 550 to 600 nm, 600 to 650 nm, 650 to 700 nm, and/or 700 to 750 nm. The term "near infrared light" or "NIR light" refers to electromagnetic radiation in a range of from about 750 nm to about 1400 nm. Individual embodiments describing NIR light as am important parameter include those in which the range of wavelengths include one or more ranges encompassing 750 to 800 nm, 800 to 850 nm, 850 to 900 nm, 900 to 950 nm, 950 to 1000 nm, 1000 to 1050 nm, 1050 to 1100 nm, 1100 to 1200 nm, 1200 to 1300 nm, and/or 1300 to 1400 nm. It should be appreciated that reference to the irradiation by NIR light or by a wavelength of near infrared (NIR) light, as used herein, is intended to connote that the irradiation includes only, or practically only, NIR light; that is, the irradiating light is devoid of any UV-Visible light wavelength.

The following listing of embodiments is intended to complement, rather than displace or supersede, the previous descriptions.

Embodiment 1

A compound comprising a near-infrared (NIR) absorbing dye having a heptamethine linkage coupled to an optionally substituted cationic heteroaryl ring moiety. It is to be understood that each of the cationic nitrogen-, oxygen-, or sulfur-containing heteroaryl moieties is considered an independent Aspect of this Embodiment. In the context of the cationic heteroaryl ring moiety, the cationic charge is distributed as a formal charge within the ring structure of the heteroaryl ring moiety, as opposed to residing on one or more of the optional substituents.

In preferred Aspects of this Embodiment, the heptamethine linkage is directly bonded to the optionally substituted cationic heteroaryl ring moiety.

In other preferred Aspects of this Embodiment, the heptamethine linkage is orthogonally coupled to the optionally substituted cationic heteroaryl ring moiety.

In some Aspects of this Embodiment, the optionally substituted cationic heteroaryl ring moiety is characterized as a charge-transfer partner of the near-infrared (NIR) absorbing dye.

In the context of this Embodiment and throughout, the term "orthogonally coupled" refers to the state where the orbitals of the heptamethine linkage of the dye and the orbitals of the optionally substituted cationic heteroaryl ring moiety are orthogonal to one another; i.e., the respective orbitals have limited or no interaction with one another, for example as a consequence of steric crowding. This lack of overlap is what is referred to by the word "orthogonal." Such "orthogonal coupling" allows for the provision of a longer-lived charge-transfer state, resulting from a "forbidden" relaxation state.

Embodiment 2

The compound of Embodiment 1, wherein the near-infrared (NIR) absorbing dye comprises a cyanine structure, a pyrylium structure, or a thiopyrylium structure, or a combination thereof. Each of these types of structures are considered independent Aspects of this Embodiment.

Embodiment 3

The compound of Embodiment 1 or 2, wherein the near-infrared (NIR) absorbing dye comprises a cyanine structure. In certain Aspects of this Embodiment, the near-infrared (NIR) absorbing dye comprising the cyanine structure, include any and all such heptamethine dyes (albeit without the optionally substituted cationic heteroaryl ring moiety for Y) that are described in U.S. Pat. Nos. 4,464,383; 5,563,028; 5,633,390; 5,973,158; 6,072,059; 6,515,811; 6,673,943; 9,610,370; and 10,280,307; each of which is incorporated by reference herein at least for its descriptions of dye portion of the claimed compounds (including backbones, substituents, and substitution patterns) and for its teachings of the methods of making and using the same.

Embodiment 4

The compound of any one of Embodiments 1 to 3, comprising a structure of:

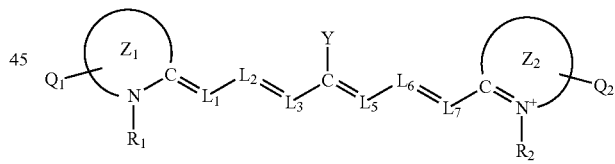

or a rotational or conformational isomer or a salt thereof wherein $L_1$, $L_2$, $L_3$, $L_5$, $L_6$, and $L_7$ are substituted or unsubstituted methines, wherein the optional substitutents are independently $C_{1-6}$ alkyl or $C_{2-6}$ alkenyl; and/or any vicinal pair of methine groups (e.g., $L_1$ and $L_3$, or $L_2$ and $L_4$, or $L_3$ and $L_5$, or $L_4$ and $L_6$, $L_5$ and $L_7$) may be linked with a $C_{2-4}$ alkylene or $C_{2-4}$ alkenylene substituent to form a 5- to 7-membered ring;

each of $Z^1$ and $Z^2$ is independently a five- or six-membered nitrogen-containing heterocyclic ring, optionally fused to another aryl or heteroaryl ring;

each of $Q_1$ and $Q_2$ is independently H or a substituent positioned on the five- or six-membered nitrogen-containing heterocyclic ring and/or the optionally fused aryl or heteroaryl ring, each optional substituent comprising an optionally substituted $C_{1-12}$ alkyl, $-[CH_2-CH_2-O-]_{1-6}R^{10}$, $C_{2-12}$ alkenyl, polyglycol optionally substituted 5- or 10-membered aryl or heteroaryl group, halo (fluoro, chloro, bromo, iodo), nitro, cyano, —$(C_{0-12}$alkyl) sulfonate or a salt thereof, —$(C_{0-12}$alkyl) sulfate or a salt thereof, —$(C_{0-12}$alkyl)phophate or a salt thereof, —$(C_{0-12}$alkyl)hydroxy, —$(C_{0-12}$alkyl)alkoxy, —$(C_{0-12}$alkyl)aryloxy, —$(C_{0-12}$alkyl)NHSO$_3$R$_{10}$ or a salt thereof, —$(C_{0-12}$alkyl)COOR$^{10}$ or a salt thereof, —$(C_{0-12}$alkyl)CON(R$^{10}$)$_2$, —$(C_{0-12}$alkyl)N(R$^{10}$)$_2$ or a salt thereof, —$(C_{0-12}$alkyl)borate, $R_1$ and $R^2$ is independently $C_{1-12}$ alkyl, —[CH$_2$—CH$_2$—O-]$_{1-6}$R$^{10}$, —$(C_{0-12}$alkyl)amino acid residue, or a 5- or 6-member ringed aryl or heteroaryl, each of which may be optionally substituted with one or more —$(C_{0-12}$alkyl)(SO$_3$)—R$^{10}$ or a salt thereof, —$(C_{0-12}$alkyl)(SO$_4$)—R$^{10}$ or a salt thereof, —$(C_{0-12}$alkyl)(PO$_4$)—R$^{10}$ or a salt thereof, —$(C_{0-12}$alkyl)OR$^{10}$, —$(C_{0-12}$alkyl)NHSO$_3$R$^{10}$ or a salt thereof, —$(C_{0-12}$alkyl)COOR$^{10}$ or a salt thereof, —$(C_{0-12}$alkyl)CON(R$^{10}$)$_2$, —$(C_{0-12}$alkyl)N(R$^{10}$)$_2$ or a salt thereof, or —$(C_{0-12}$alkyl)borate or borate ester;

$R^{10}$ is independently H or $C_{1-6}$ alkyl; and

Y is the optionally substituted cationic heteroaryl ring moiety.

It should be appreciated that while Y is shown here as being in the $L_4$ position (i.e., between the $L_3$ and $L_5$ methines), and is preferably positioned there, in other Aspects of this Embodiment, Y can be alternatively positioned on any of the $L_1$, $L_2$, $L_3$, $L_4$, $L_5$, $L_6$, or $L_7$ positions. Likewise, other Aspects of this Embodiment include all geometric and rotational isomers of the provided structure.

Likewise, it should be appreciated that while $Q_1$, $Q_2$, $R_1$, and $R_2$ are defined in terms of specific optional substituents, and Y is defined merely as "optionally substituted," in some Aspects of this Embodiment, the optional substituents may also include those defined elsewhere herein as Fn. In this regard, any one or more of these Fn substituents is considered to be selected independently, as if listed individually.

In some Aspects of this Embodiment, $Z_1$ and $Z_2$ are the same. In other Aspects of this Embodiment, $Z_1$ and $Z_2$ are different.

Embodiment 5

The compound of Embodiment 4, wherein the five- or six-membered nitrogen-containing heterocyclic ring of $Z_1$ and $Z_2$ independently comprise a pyrrole ring, imidazole ring, isothiazole ring, isoxazole ring, oxadiazole ring, oxazole ring, pyrazole ring, pyrimidyl, thiazole ring, selenazole ring, thiadiazole ring, triazole ring, or a pyridine ring. Again, it is understood that in certain Aspects of this Embodiment, $Z_1$ and $Z_2$ are the same. In other Aspects, $Z_1$ and $Z_2$ are different. It should also be understood throughout that reference to a five- or six-membered nitrogen-containing ring includes these five- and six-membered nitrogen-containing rings as separated Aspects of any Embodiment cited herein.

Embodiment 6

The compound of Embodiment 4 or 5, wherein the five- or six-membered nitrogen-containing heterocyclic ring of $Z_1$ and $Z_2$ is independently fused to a phenyl, naphthyl, pyridinyl, quinolinyl, quinoxalinyl, N-alkyl-benzoindolenine, dibenzofuranyl, or dibenzothiophenyl.

Embodiment 7

The compound of Embodiment 4 or 5, wherein $Z_1$ and $Z_2$ independently comprise a benzimidazole ring, benzindole ring, benzoindolenine ring, benzoxazole ring, benzothiazole ring, furopyrrole ring, imidazole ring, imidazoquinoxaline ring, indolenine ring, indolizine ring, isoxazole ring, naphthimidazole ring, naphthothiazole ring, naphthoxazole ring, oxazolocarbazole ring, oxazole ring, oxazolodibenzofuran ring, pyrrolopyridine ring, pyridine ring, quinoline ring, quinoxaline ring, thiazole ring, or naphthoimidazole ring.

Embodiment 8

The compound of any one of Embodiments 4 to 7, whose methines not bonded to Y are otherwise not substituted. For example, in some Aspects of this Embodiment, where Y is in the $L_4$ position, $L_1=L_2=L_3=L_5=L_6=L_7=CH$. In other Aspects, where where Y is in the $L_1$ position, $L_2=L_3=L_4=L_5=L_6=L_7=CH$. In other Aspects, where where Y is in the $L_2$ position, $L_1=L_3=L_4=L_5=L_6=L_7=CH$. In other Aspects, where where Y is in the $L_3$ position, $L_1=L_2=L_4=L_5=L_6=L_7=CH$.

Embodiment 9

The compound of any one of Embodiments 4 to 8, wherein one of $L_1$ and $L_3$, or $L_2$ and $L_4$, or $L_3$ and $L_5$, or $L_4$ and $L_6$, or $L_5$ and $L_7$ are linked with a $C_{2-4}$ alkylene substituent to form a 5- to 7-membered ring. Each of these Aspects of this Embodiment is considered independently and combinable with any Aspect or Embodiment of the preceding or following Embodiments.

In an exemplary Aspect of this Embodiment, the compound comprises a structure of:

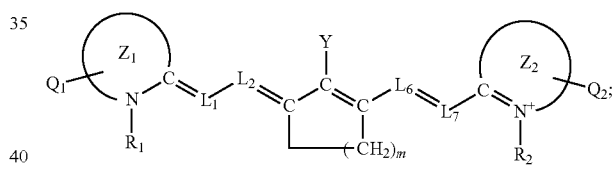

or a rotational or conformational isomer or a salt thereof; where $L_1$, $L_2$, $L_3$, $L_4$, $L_5$, $L_6$, $L_7$, $Q_1$, $R_1$, Y, $Z_1$, are defined in any of the definitions as set forth elsewhere herein in any combination or permutations and m is 1, 2, or 3.

Embodiment 10

The compound of any one of Embodiments 4 to 9, comprising a structure of:

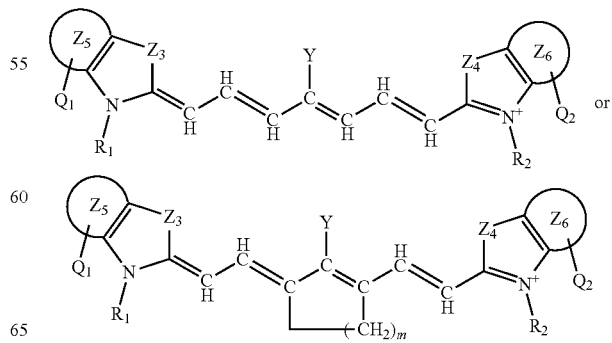

or a rotational or conformational isomer or a salt thereof wherein each of $Z_3$ and $Z_4$ is independently —$CR^{11}R^{12}$, —$NR^{11}$, —O—, —S— or —Se— (each of $Z_3$ and $Z_4$ is independently preferably —$CR^{11}R^{12}$, —$NR^{11}$, —O— or —S—, each of $Z_3$ and $Z_4$ is independently more preferably is —$CR^{11}R^{12}$; —O— or —S, each of $Z_3$ and $Z_4$ is independently further preferably is —$CR_{11}R_{12}$ or —O—, and each of $Z_3$ and $Z_4$ is independently most preferably —$CR^{11}R^{12}$);

each of $Z_5$ and $Z_6$ is independently preferably phenyl, naphthyl, pyridinyl, quinolinyl, quinoxalinyl, N-alkyl-benzoindolenine, dibenzofuranyl, or dibenzothiophenyl, each of $R^{11}$ and $R^{12}$ is independently a $C_{1-6}$ alkyl, preferably methyl; and $Q_1$ and $Q_2$ are independently, preferably H, —COOH or a salt thereof, or —$SO_3H$ or a salt thereof.

Embodiment 11

The compound of any one of Embodiments 4 to 10, comprising a structure of:

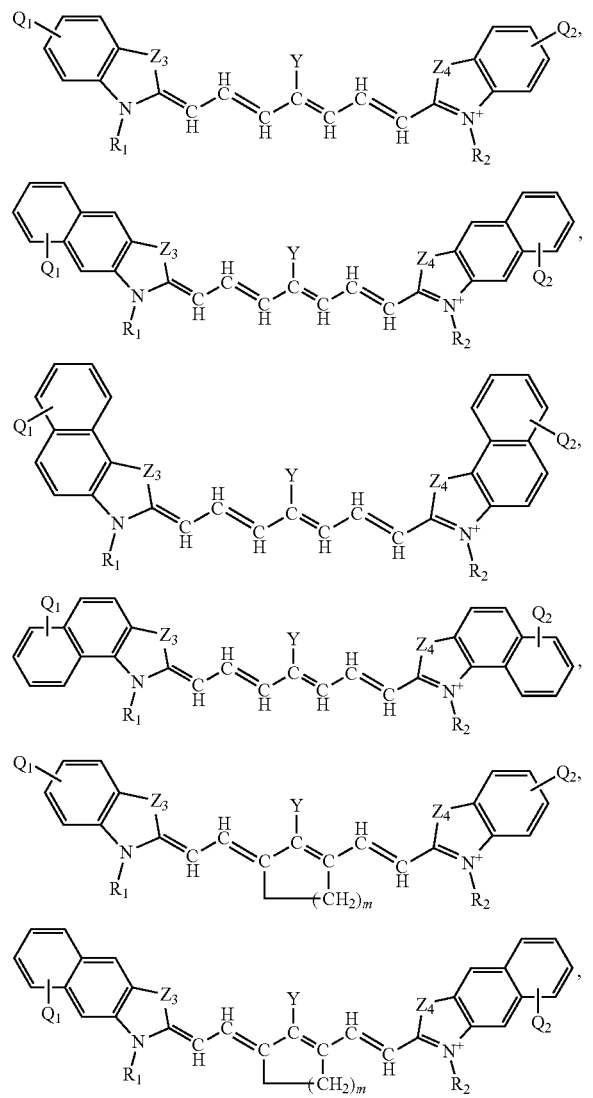

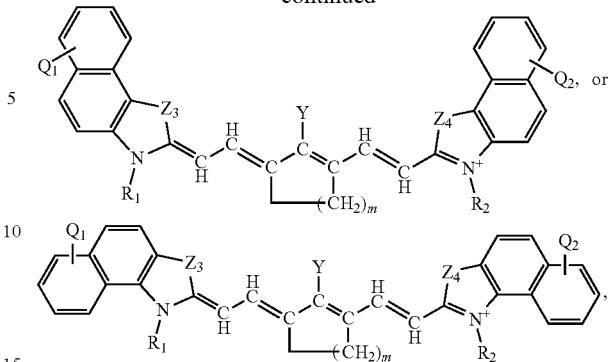

or a rotational or conformational isomer or a salt thereof wherein each of $Z_3$ and $Z_4$ is independently —$CR^{11}R^{12}$, —$NR^{11}$, —O—, —S— or —Se— (each of $Z_3$ and $Z_4$ is independently preferably —$CR^{11}R^{12}$, —$NR^{11}$, —O— or —S—, each of $Z_3$ and $Z_4$ is independently more preferably is —$CR^{11}R^{12}$, —O— or —S, each of $Z_3$ and $Z_4$ is independently further preferably is —$CR^{11}R^{12}$ or —O—, and each of $Z_3$ and $Z_4$ is independently most preferably —$CR^{11}R^{12}$);

each of $R^{11}$ and $R^{12}$ is independently a $C_{1-6}$ alkyl, preferably methyl;

m=1, 2, or 3; and $Q_1$ and $Q_2$ are independently, preferably H, —COOH or a salt thereof, or —$SO_3H$ or a salt thereof.

In certain independent Aspects of this Embodiment, the fused naphthalene moiety may be replaced with an optionally substituted quinolinyl, quinoxalinyl, N-alkyl-benzoindolenine, dibenzofuranyl, or dibenzothiophenyl ring.

Embodiment 12

The compound of any one of claims 4 to 11, comprising a structure of:

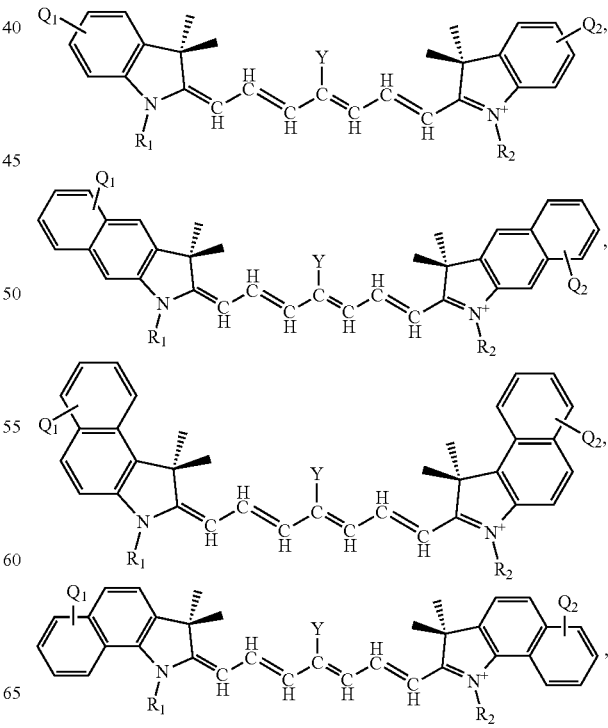

-continued

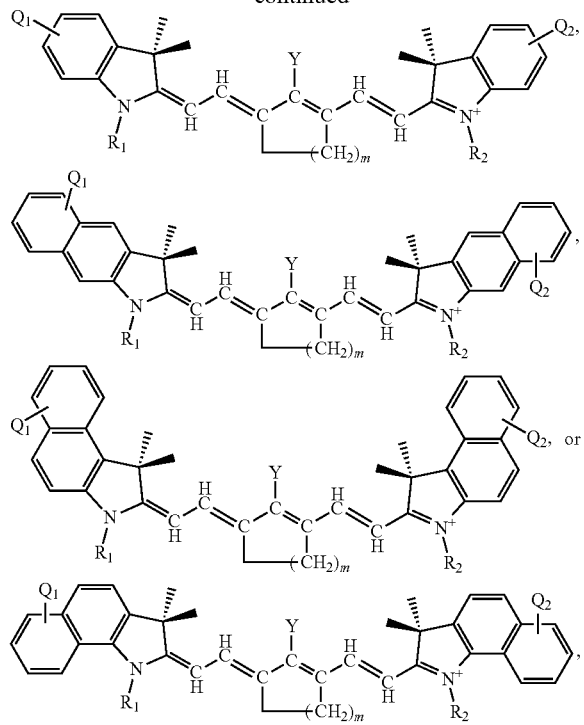

or a rotational or conformational isomer or a salt thereof where $R_1$ and $R^2$ are independently —$(C_{1-12}$alkyl$)(SO_3)$H or a salt thereof or —$(C_{1-12}$alkyl$)$COOH or a salt thereof. Each of these structures represents an independent Aspect of this Embodiment.

In certain independent Aspects of this Embodiment, the fused naphthalene moiety may be replaced with an optionally substituted quinolinyl, quinoxalinyl, N-alkyl-benzoindolenine, dibenzofuranyl, or dibenzothiophenyl ring.

Embodiment 13

The compound of Embodiment 1, wherein the near-infrared (NIR) absorbing dye comprises a pyrylium dye or a thiopyrylium dye. In certain Aspects of this Embodiment, the near-infrared (NIR) absorbing dye comprising the pyrylium dye or the thiopyrylium dye includes any and all such heptamethine dyes (albeit without the optionally substituted cationic heteroaryl ring moiety) that are described in U.S. Pat. No. 4,283,475 that are incorporated by reference for its teachings of these types of dyes, and the ability to functionalize and make these dyes.

Embodiment 14

The compound of Embodiment 13, comprising a structure of:

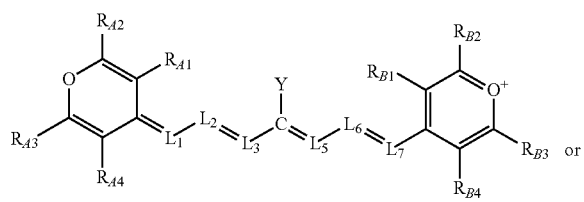

-continued

[structure showing thiopyrylium dye with $R_{A1}$, $R_{A2}$, $R_{A3}$, $R_{A4}$, $R_{B1}$, $R_{B2}$, $R_{B3}$, $R_{B4}$, S, S$^+$, Y, $L_1$–$L_7$]

or a rotational or conformational isomer or a salt thereof; wherein $L_1$, $L_2$, $L_3$, $L_5$, $L_6$, and $L_7$ are substituted or unsubstituted methines, wherein the optional substitutents are independently $C_{1-6}$ alkyl or $C_{2-6}$ alkenyl; or $L_1$ and $L_3$, or $L_3$ and $L_5$, or $L_5$ and $L_7$ may be linked with $C_{2-4}$ alkylene or $C_{2-4}$ alkenylene substituents;

$R_{A1}$, $R_{A2}$, $R_{A3}$, $R_{A4}$, $R_{B1}$, $R_{B2}$, $R_{B3}$, and $R_{B4}$ are each independently H, deutrium, or tritium, an $C_{1-12}$ alkyl, —[$CH_2$—$CH_2$—$O$-$]_{1-6}R^{10}$, $C_{2-12}$ alkenyl, polyglycol optionally substituted 5- or 10-membered aryl or heteroaryl group, halo (fluoro, chloro, bromo, iodo), nitro, cyano, —($C_{0-12}$alkyl) sulfonate or a salt thereof, —($C_{0-12}$alkyl) sulfate or a salt thereof, —($C_{0-12}$alkyl)phophate or a salt thereof, —($C_{0-12}$alkyl)hydroxy, —($C_{0-12}$alkyl)alkoxy, —($C_{0-12}$alkyl)aryloxy, —($C_{0-12}$alkyl)NHSO$_3$R$_{10}$ or a salt thereof, —($C_{0-12}$alkyl)COOR$^{10}$ or a salt thereof, —($C_{0-12}$alkyl)CON(R$^{10}$)$_2$, —($C_{0-12}$alkyl)N(R$^{10}$)$_2$ or a salt thereof, —($C_{0-12}$alkyl)borate;

n is independently 0, 1, 2, 3, or 4, preferably 2;

$R^{10}$ is independently H or $C_{1-6}$ alkyl; and

Y is the optionally substituted heteroaryl ring moiety.

It should be appreciated that while Y is shown here as being in the $L_4$ position (i.e., between the $L_3$ and $L_5$ methines), and is preferably positioned there, in other Aspects of this Embodiment, Y can be alternatively positioned on any of the $L_1$, $L_2$, $L_3$, $L_4$, $L_5$, $L_6$, or $L_7$ positions. Likewise, other Aspects of this Embodiment include all geometric and rotational isomers of the provided structure.

Likewise, it should be appreciated that while Y is defined merely as "optionally substituted," the optional substituents may also include those defined elsewhere herein as Fn. In this regard, any one or more of these Fn substituents is considered to be selected independently, as if listed individually. Also, $R_{A1}$, $R_{A2}$, $R_{A3}$, $R_{A4}$, $R_{B1}$, $R_{B2}$, $R_{B3}$, and $R_{B4}$ may also independently be any one or more the these Fn substituents.

In some Aspects of this Embodiment, $Z_1$ and $Z_2$ are the same. In other Aspects of this Embodiment, $Z_1$ and $Z_2$ are different.

Embodiment 15

The compound of Embodiment 14, whose methines not bonded to Y are otherwise not substituted. For example, in some Aspects of this Embodiment, where Y is in the $L_4$ position, $L_1$=$L_2$=$L_3$=$L_5$=$L_6$=$L_7$=CH. In other Aspects, where where Y is in the $L_1$ position, $L_2$=$L_3$=$L_4$=$L_5$=$L_6$=$L_7$=CH. In other Aspects, where where Y is in the $L_2$ position, $L_1$=$L_3$=$L_4$=$L_5$=$L_6$=$L_7$=CH. In other Aspects, where where Y is in the $L_3$ position, $L_1$=$L_2$=$L_4$=$L_5$=$L_6$=$L_7$=CH.

In an exemplary Aspect of this Embodiment, the compound comprises a structure of:

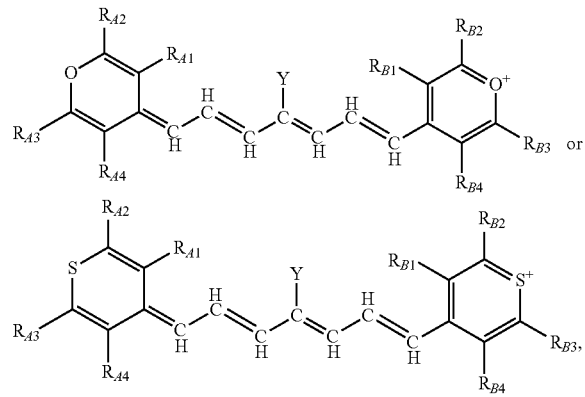

or a rotational or conformational isomer or a salt thereof.

Embodiment 16

The compound of Embodiment 14, wherein one of $L_1$ and $L_3$, or $L_2$ and $L_4$, or $L_3$ and $L_5$, or $L_4$ and $L_6$, or $L_5$ and $L_7$ are linked with a $C_{2-4}$ alkylene substituent to form a 5- to 7-membered ring. Each of these Aspects of this Embodiment is considered independently and combinable with any Aspect or Embodiment of the preceding or following Embodiments.

In an exemplary Aspect of this Embodiment, the compound comprises a structure of:

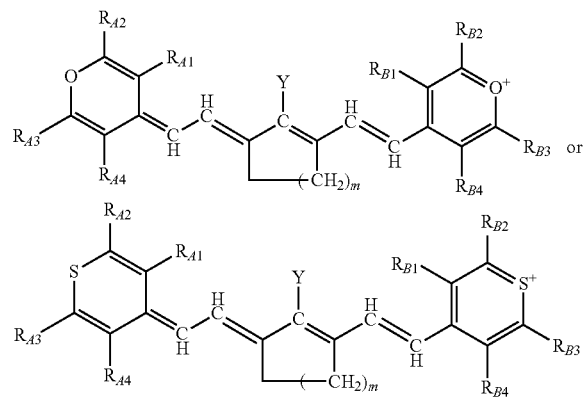

or a rotational or conformational isomer or a salt thereof; where m is 1, 2, or 3.

Embodiment 17

The compound of any one of Embodiments 14 to 16, wherein $R_{A1}$, $R_{A4}$, $R_{B1}$, and $R_{B4}$ are H, or an isotope thereof, and $R_{A2}$, $R_{A3}$, $R_{B2}$, and $R_{B3}$ are aryl, heteroaryl, or branched alkyl preferably phenyl, pyridinyl, or tert-butyl.

Embodiment 18

The compound of any one of Embodiments 1 to 17, wherein the optionally substituted cationic heteroaryl ring moiety, preferably the optionally substituted cationic heteroaryl ring, is directly bonded to the heptamethine linkage; i.e., no additional linking groups. In certain Aspects of this Embodiment, the optionally substituted cationic nitrogen-containing heteroaryl ring is bonded to the heptamethine linkage by a C—C bond or a C—N bond. In certain Aspects of this Embodiment, the optionally substituted cationic oxygen- or sulfur-containing heteroaryl ring is bonded to the heptamethine linkage by a C—C bond Again, it should be appreciated that in the optionally substituted cationic heteroaryl ring moiety, the optionally substituted cationic charge is distributed in the ring structure of the nitrogen-, oxygen-, or sulfur-containing heteroaryl ring moiety.

Embodiment 19

The compound of any one of Embodiments 1 to 18, wherein the optionally substituted cationic heteroaryl ring moiety comprises an optionally substituted acridinium, benzoxazolium, benzothiazolium, imidazolium, isoxazolium, isoquinolinium, isothiazolium, naphthoimidazolium, naphthothiazolium, naphthoxazolium, oxazolium, pyrazinium, pyrazolium, pyridimium, pyridinium, quinolinium, tetrazinium, tetrazolium, thiazolium, triazinium, triazolium, benzopyrazinium, benzopyridimium, benzopyridinium, naphthopyrazinium, naphthopyridimium, benzopyridinium, benzotriazinium, naphthotriazinium moiety, pyrylium, chromenylium, xanthylium moiety, thiopyrylium, thiochromenylium, or thioxanthylium moiety.

In certain Aspects of this Embodiment, the optional substituents comprise any one or more of the functional group Fn a set forth elsewhere herein. In this regard, any one or more of these Fn substituents is considered to be selected independently, as if listed individually.

Embodiment 20

The compound of any one of Embodiments 1 to 19, wherein the optionally substituted cationic heteroaryl ring moiety comprises a structure:

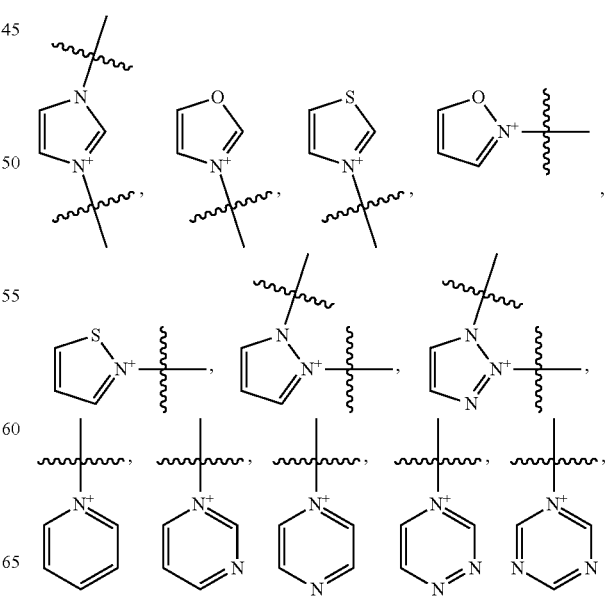

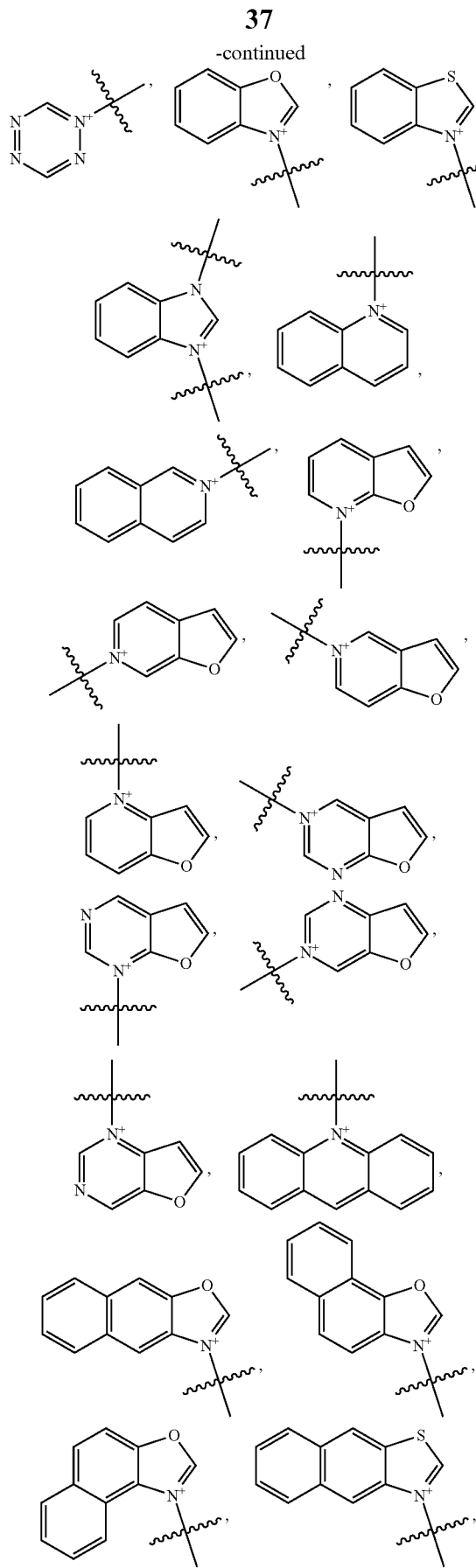

Embodiment 21

The compound of any one of Embodiments 1 to 20, wherein the compound comprises at least one cationic group and has a net neutral or net positive charge, wherein at least one associated cationic group, groups or moieties is charge balanced by an anionic counter ion. In certain Aspects of this Embodiment, the anionic counter ions are halide anions (e.g., fluoride, chloride, bromide, and/or iodide), or other inorganic anions (e.g., perchlorate, tetrafluoroborate, hexafluorophosphate, sulfate, hydrogensulfate and/or nitrate) or organic anions (e.g., organic anions such as trifluoroacetate, trichloroacetate, triflate, mesylate, and/or p-toluenesulfonate ions).

In some Aspects of this Embodiment, the dye portion of the compound may also have least one associated cationic group or moiety that are internally charged balanced.

Where one or more substituents are anionic (for example, carboxylate or sulfonate anions), they may have associated counter cations, such as alkali metal cations, such as Li$^+$, Na$^+$, or K$^+$. The choice of counter cations or anions should not be limited.

Embodiment 22

The compound of any one of Embodiments 1 to 21, wherein the compound comprises, is substituted with, or is conjugated to at least one isotope of carbon, chlorine, fluorine, hydrogen, iodine, nitrogen, or oxygen enriched above its natural abundance. In certain Aspects of this Embodiment, the isotope is a radioisotope. Examples of isotopes suitable for inclusion in the compounds described herein include and are not limited to $^2$H, $^3$H, $^{11}$C, $^{13}$C, $^{14}$C, $^{36}$Cl, $^{18}$F, $^{123}$I, $^{125}$I, $^{13}$N, $^{15}$N, $^{15}$O, $^{17}$O, $^{18}$O, $^{32}$P, and $^{35}$S.

In some Aspects of this Embodiment, the degree of enrichment is at least 5 time, at least 10 times, at least 100 time, or at least 1000 times (depending on the nature of the isotope and its natural abundance) above its natural abundance up to completely substituted in that isotope.

Embodiment 23

The compound of any one of claims 1 to 22, that exhibits a local $\lambda_{max}$ for light absorption in a range of from 750 nm to 1400 nm. In independent Aspects of this Embodiment, this range can be defined in terms of from 750 nm to 800 nm, from 800 nm to 850 nm, from 850 nm to 900 nm, from 900 nm to 950 nm, from 950 nm to 1000 nm, from 1000 nm to 1050 nm, from 1050 nm to 1100 nm, from 1100 nm to 1150 nm, from 1150 nm to 1200 nm, from 1200 nm to 1250 nm, from 1250 to 1300 nm, from 1300 to 1350 nm, from 1350 nm to 1400 nm, or in a range comprising two of more of these foregoing ranges, for example from 800 nm to 1100 nm.

Embodiment 24

The compound of any one of claims 1 to 23, that generates singlet oxygen, when the compound is irradiated in the presence of 02 at a wavelength in a range of from 750 nm to 1400 nm. In independent Aspects of this Embodiment, this range can be defined in terms of from 750 nm to 800 nm, from 800 nm to 850 nm, from 850 nm to 900 nm, from 900 nm to 950 nm, from 950 nm to 1000 nm, from 1000 nm to 1050 nm, from 1050 nm to 1100 nm, from 1100 nm to 1150 nm, from 1150 nm to 1200 nm, from 1200 nm to 1250 nm, from 1250 to 1300 nm, from 1300 to 1350 nm, from 1350 nm to 1400 nm, or in a range comprising two of more of these foregoing ranges, for example from 800 nm to 1100 nm.

These compounds, and their ability to generate free radicals or singlet oxygen when irradiated by NIR light in the presence of oxygen, make them attractive for use in a range of applications. In other aspects, the presence of the optionally substituted cationic heteroaryl ring moiety alters the photophysics of the molecules making them also attractive for use as simple dyes.

Embodiment 25

A composition comprising a compound of any one of Embodiments 1 to 24 dissolved or suspended in a solvent, or are in contact with a solvent comprising a deuterated solvent. In certain Aspects of this Embodiment, the deuterated solvent is or comprises deuterated chloroform, dimethyl sulfoxide, methanol, ethanol, tetrahydrofuran, or water.

Embodiment 26

An optical filter comprising a transparent support and at least one filter layer, wherein the filter layer contains a compound of any one of Embodiments 1 to or 24 or composition of Embodiment 25. In some Aspects of this Embodiment, the transparent support comprises a polymer film. Other Aspects of this Embodiment comprise plasma display panels having a display surface covered with such optical filters, preferably, wherein the optical filter is directly attached to the display surface. Such optical filters and display panels are disclosed, for example, in U.S. Pat. No. 6,515,811, which is incorporated by reference herein for its teachings of such devices.

Embodiment 27

A method for imaging a biosubstrate or a living cell, comprising the step of interacting the compound of any one of Embodiments 1 to 24 or composition of Embodiment 25 with the biosubstrate or the living cell; and observing said biosubstrate or living cell, for example, with a confocal laser scanning microscope. In certain Aspects of this Embodiment, the bio-substrate is a DNA, a protein, or a liposome. Other independent Aspects of this Embodiment include the stains useful in these methods. In other Aspects of this Embodiment, the imaging is done in vivo. In still other Aspects of this Embodiment, the imaging is done ex vivo. Such methods are set forth in U.S. Pat. No. 8,735,601, which is incorporated by reference herein for its teachings of such methods.

Embodiment 28

A method comprising contacting a biological sample with a compound of any one of Embodiments 1 to 24 or composition of Embodiment 25; and irradiating the biological sample by application of light having a wavelength or range of wavelengths in the near-infrared range.

In certain Aspects of this Embodiment, the method further comprises detecting fluorescence of the irradiated biological sample, wherein fluorescence indicates presence of the compound in the biological sample.

In certain Aspects of this Embodiment, the compound comprises a biomolecule capable of binding to a target present or suspected of being present within the biological sample and fluorescence indicates the target is present in the biological sample, the method further comprising removing unbound compound from the biological sample prior to obtaining the image.

In certain Aspects of this Embodiment, the method comprises irradiating the biological sample comprises irradiating a target area of the subject with near-infrared radiation; and detecting fluorescence comprises obtaining an image of the irradiated target area, wherein fluorescence in the image indicates presence of the target in the target area.

In certain Aspects of this Embodiment, the target is a tumor and the target area is an area in which the tumor is located. In certain Aspects of Embodiment, the method further comprising excising fluorescent tumor cells from the target area.

In certain Aspects of this Embodiment, the method further comprises, irradiating the compound with near-infrared radiation in the presence of oxygen, such that the irradiating generates singlet oxygen known to be detrimental to cancer cells.

Such methods in this Embodiment are set forth in U.S. Pat. Nos. 9,610,370 and 10,280,307, which is incorporated by reference herein for their teachings of such methods.

EXAMPLES

The following Examples are provided to illustrate some of the concepts described within this disclosure. While each Example is considered to provide specific individual embodiments of composition, methods of preparation and use, none of the Examples should be considered to limit the more general embodiments described herein.

In the following examples, efforts have been made to ensure accuracy with respect to numbers used (e.g. amounts, temperature, etc.) but some experimental error and deviation should be accounted for. Unless indicated otherwise, temperature is in degrees C., pressure is at or near atmospheric.

Example 1: Materials and Methods

Example 1.1

IR-1061 tetrafluoroborate and dry pyridine were purchased from commercial sources and used as supplied. Deuterated chloroform was purchased from commercial sources and filtered through a neutral alumina plug prior to use to neutralize and dry the solvent. Irradiations at 980 nm were performed using a 1 watt/cm$^2$ infrared diode laser at 980 nm coupled to a PSU-III-FDA power supply. Irradiations at 1064 nm were performed using an Nd:YAG laser at 1.8 W/cm$^2$. Absorbance spectra were obtained using an Agilent CARY 60 UV-Vis for spectra below 1000 nm, and a Cary 5000 UV-VIS-NIR for spectra above 1000 nm. Mass spectrometry characterization was performed via MALDI using a BRUKER MALDI/TOF Autoflex Speed and a Waters LCT Premier XE Electrospray TOF. 1H NMR spectra were obtained using a Varian 600 MHz Spectrometer.

Example 1.2: Calculations

Computation was performed using the SPARTAN interface with calculations performed using the B3LYP functional and the 6-31G basis set. These calculations were performed in accordance with previous calculations performed on the 9-mesityl-10-methylacrindium dyad.1 Higher levels of computation (using the MO6 functional and larger basis sets) were performed on the BODIPY dyads to check for differences, and none were observed. Given the large size of the IR-1061 dye and the lack of significant differences in higher level calculations, we felt that B3LYP and 6-31G were the most appropriate selection.

Example 1.3: Irradiation Experiments

Dye was dissolved in deuterated solvent at a concentration that would produce an absorbance near 1 at 980 nm. This was calculated using extinction coefficients determined by absorbance measurements of the dye alone. The IR-1061-acridinium irradiation in water was an exception, as the concentration was kept lower to ensure solubility. Dye solution was split into two aliquots and added to two 1 cm by 1 cm quartz cuvettes purchased from Starna. The absorption spectra were taken for both cuvettes (to ensure the pre-irradiation sample looked the same in both cases), and subsequently one cuvette was irradiated while the other was kept in the dark. A stir bar was used to ensure proper mixing during irradiation. After irradiation, the absorbance of both solutions was again evaluated. Figures shown without a dark control still had one, however, no significant change was observed in the irradiated samples so the dark control trace was unnecessary and therefore not included. For the 1064 nm irradiation, the dye was dissolved at a slightly higher concentration to an absorbance of approximately 1.5 at 1064 nm and irradiated for 5 minutes. At this point significant photobleaching of the dye was observed, so additional irradiation was not performed.

The freeze-pump-thaw (FPT) experiment was carried out as follows. Dye was dissolved in deuterated chloroform and added to a FPT that apparatus. Three consecutive freeze-pump-thaw cycles were carried out to a pressure of less than 200 mm Hg, at which point the solution was transferred under vacuum to the arm of the apparatus containing a fused 1 cm by 1 cm quartz cuvette (Starna). Irradiation and subsequent absorption measurements were carried out in the sealed cuvette.

Example 1.4: Comparative Quantum Yield Experiments

Phenalenone, a highly efficient singlet oxygen generator with a known singlet oxygen quantum yield of 0.97 in chloroform was used to benchmark the efficiency of IR-1061-acridinium singlet oxygen generation in chloroform. A solution of phenalenone at an absorbance of 0.30 at 365 nm was generated that also contained DPBF at an absorbance of approximately 1.0. This solution was irradiated for 30 seconds using a 365 nm variable power LED (3-300 mW, Thor labs) at 30 mW/cm$^2$. The percent decrease in DPBF signal at 415 nm was calculated, taking into account any background from phenalenone. This was done in triplicate. A similar experiment was then run using IR-1061-acridinium. A solution containing the dye at an absorbance of 0.30 at 1064 and DPBF at an absorbance of approximately 1.0 was irradiated for 30 seconds using a 1064 nm Nd:YAG laser with a power output of 1.8 W/cm$^2$. The percent decrease in DPBF signal at 415 nm was then calculated, taking into account any background from IR-1061-acridinium. This was also done in triplicate.

The percent decrease attributed to phenalenone was calculated to be 0.53 and the percent decrease attributed to IR-1061-acridinium was calculated to be 0.29. To account for the difference in photon flux at these two wavelengths, the ratio of the photon flux was calculated, where the photon flux was described by the following equation: $PF=I*\lambda/(h*c*Na)$. PF stands for photon flux, I is the irradiation intensity, $\lambda$ is the irradiation wavelength, his Planck's constant, c is the speed of light and Na is Avogadro's number. The ratio of the photon flux was simplified to $PFR=(I_{Phe}*\lambda_{Phe})/(I_R*\lambda_{Ir})=(0.03\ W/cm^2*365\ nm)/(1.8\ W/cm^2*1064\ nm)=0.006$. Considering this difference in photon flux and phenalenone's known quantum yield of singlet oxygen generation of 0.97, this yielded a relative quantum yield of about 0.003, or 0.3%.

Figure 2:
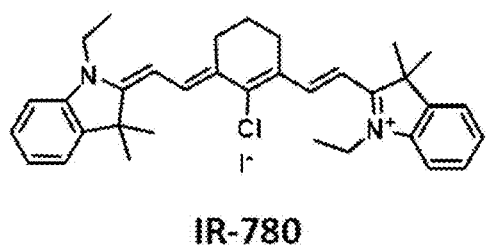
FIG. 2 illustrates representative structures evaluated in this work.
Figure 2:
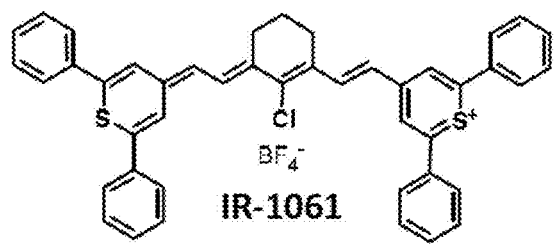
Figure 2:
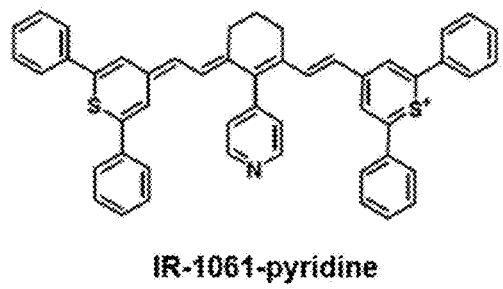
Figure 2:
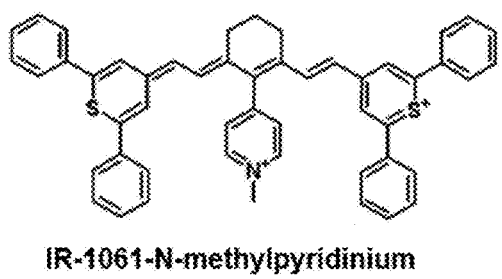
Figure 2:
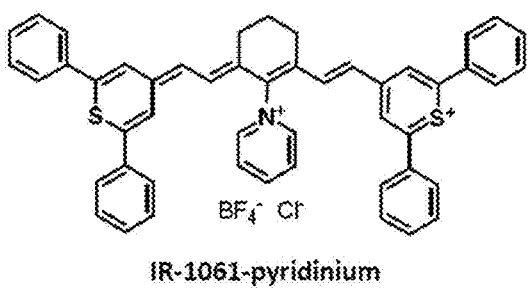
Figure 2:
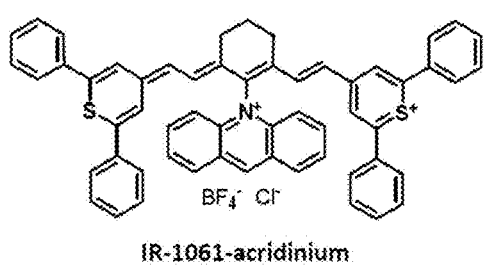
Figure 2:
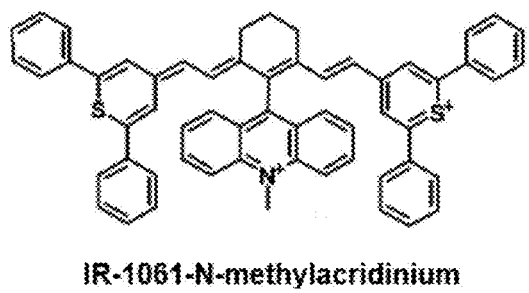
Figure 2:
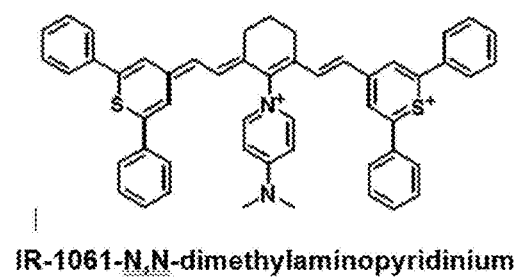

Example 1.5: IR-1061-pyridinium Synthesis (see FIG. 2)

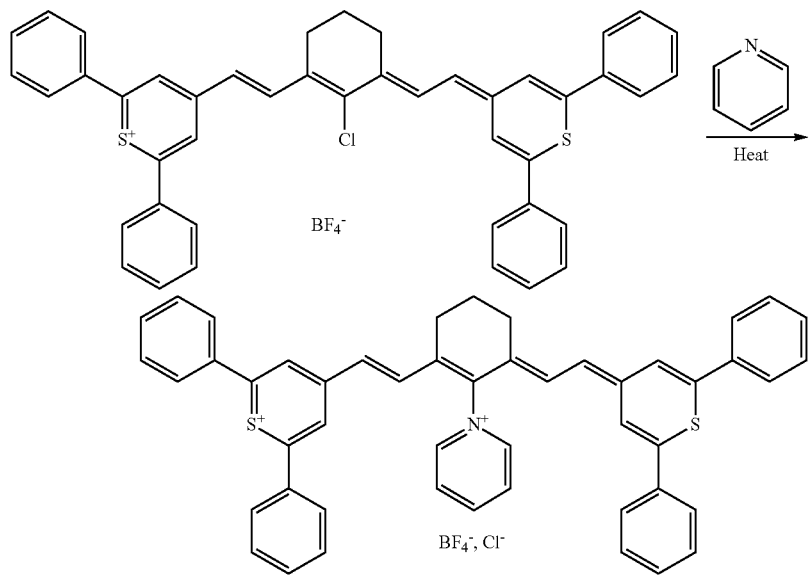

Figure 3:
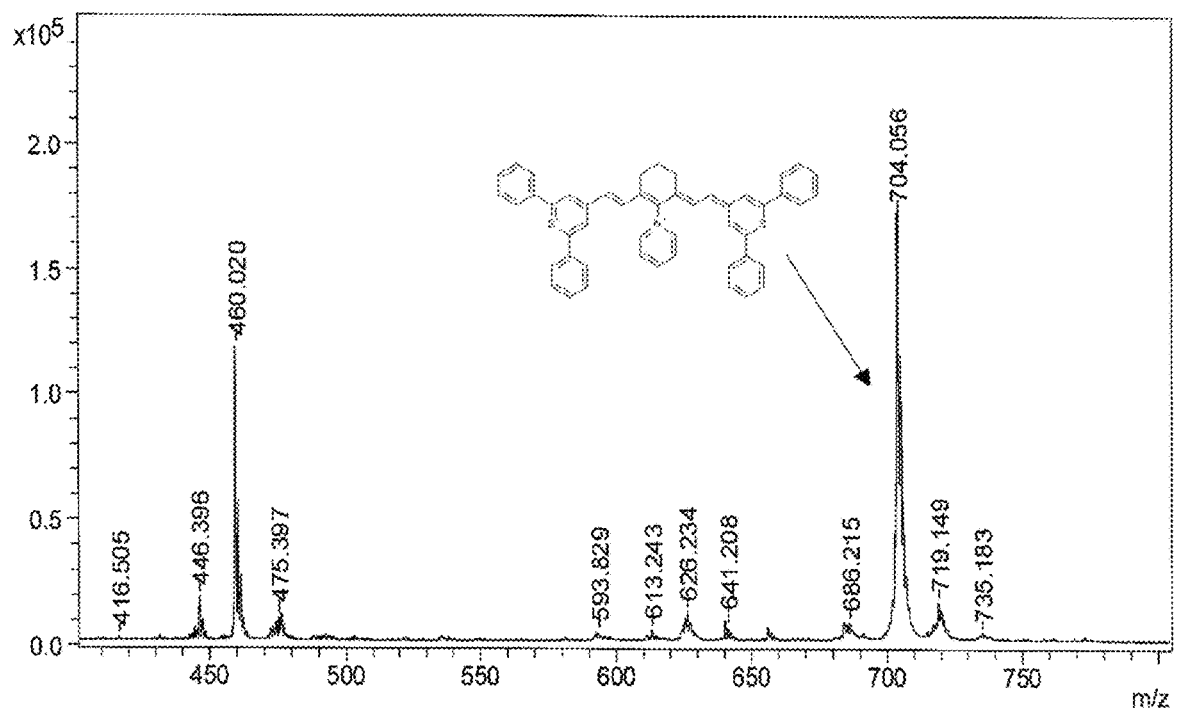
FIG. 3 shows a MALDI spectrum of slightly impure IR-1061 pyridinium. When isolated, the major impurity at 460 amu has no absorbance in the NIR.

A 10 mL flame-dried round-bottom flask was charged with a stir bar and 25 mgs of IR-1061, to which 1 mL of dry pyridine was added. The reaction was heated to boiling under argon and removed from heat once the solution transitioned from dark red to greenish-brown. At this point the compound was purified by silica gel chromatography using a 0-5% MeOH in dichloromethane (DCM) gradient. The product could not be cleanly purified due to decomposition during purification. All other attempted purification conditions gave the same result. Due to low solubility and contaminating species, an interpretable NMR was never obtained, however, a reasonably clean mass spectrometry trace was obtained. MS (MALDI-TOF): (m/z) calculated for $C_{49}H_{38}NS_2+$: 704.24 (m−1). Observed 704.056 (m−1, presumably due to loss of a proton to alleviate the dual positive charge) (FIG. 3).

Example 1.6: IR-1061-C-Bonded-Pyridinium Synthesis

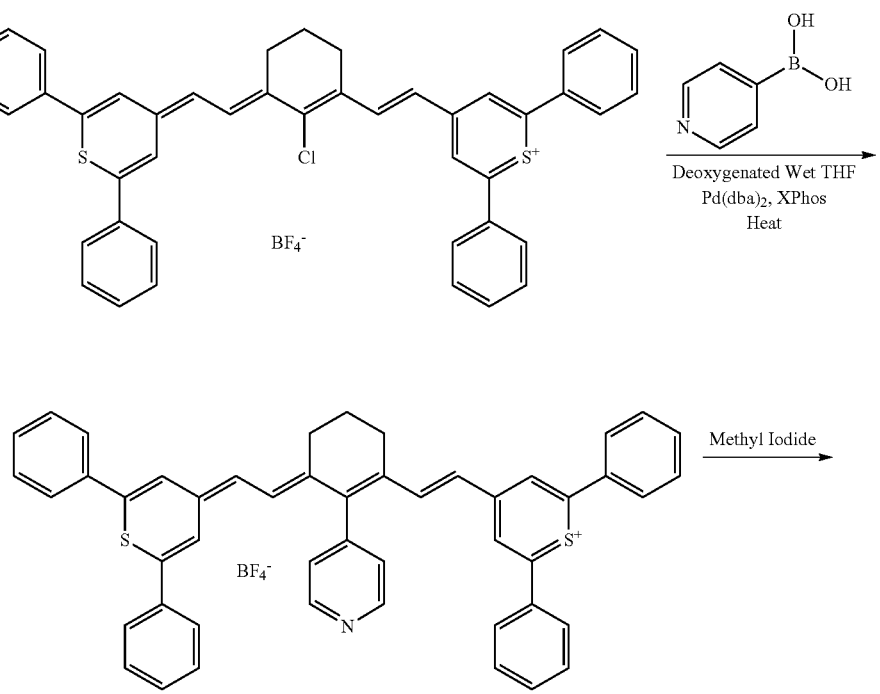

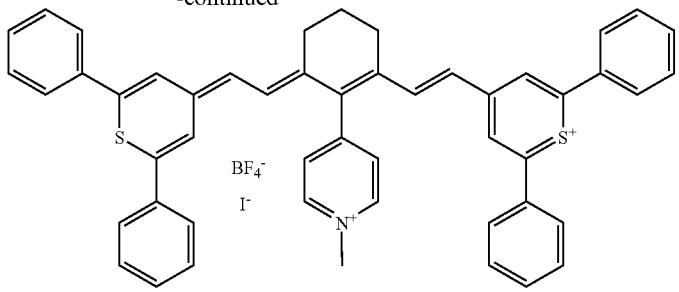

Example 1.7: IR-1061-acridinium Synthesis

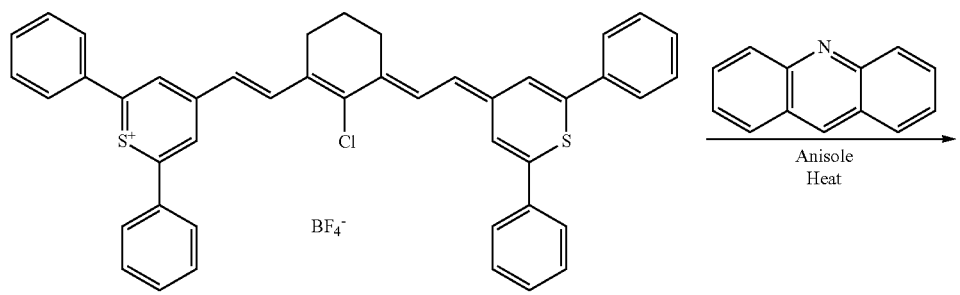

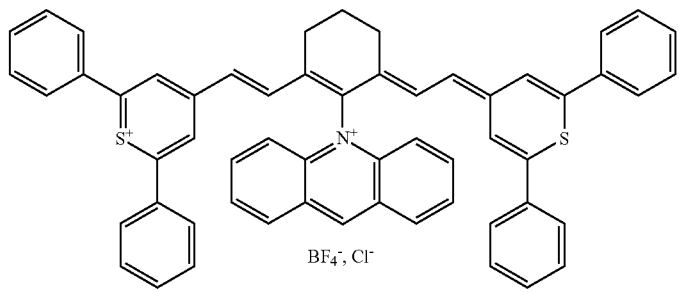

Figure 4:
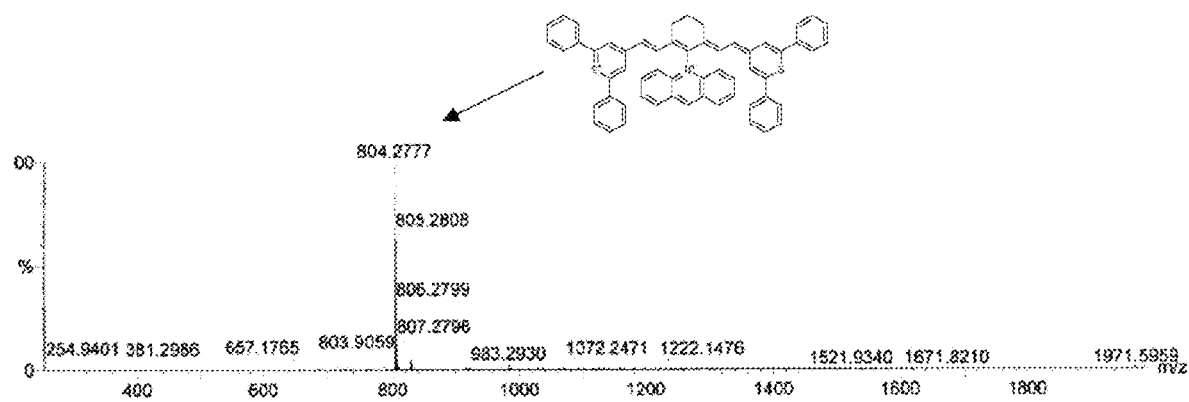
FIG. 4 shows an ESI/TOF spectrum of IR-1061-acridinium.

A 10 ml round-bottom flask was charged with a stir bar, 25 mgs of IR-1061 (1 equivalent), and 60 mgs of acridine (10 equivalents). Two milliliters of anisole were added, and the reaction was heated to boiling under argon. It was removed from heat once the color change from red to a yellow hued brown. Further heating led to formation of a green decomposition product. The reaction mixture was loaded onto a silica plug, and after eluting the anisole and any nonpolar compounds with DCM, a polar fraction containing the dye of interest was eluted with 5% MeOH in DCM. After pumping down, this polar fraction was resuspended in DCM and loaded onto a silica gel column, which was eluted with a 0-2% MeOH in DCM gradient. 20 mgs of pure product were collected as a brown-yellow compound, giving a percent yield of 64%. $^1$H-NMR: 7.75 (m, 2H), 7.68-7.60 (m, 12H), 7.52-7.42 (m, 14H), 6.99 (t, 2H) 6.91 (d, 2H), 6.65 (t, 2H), 6.59 (d, 2H), 6.28 (m, 1H), 2.84 (t, 2H), 2.56 (t, 2H), 1.95 (m, 2H) MS (ESI-TOF): (m/z) calculated for $C_{57}H_{42}NS_2$+: 804.275 (m−1). Observed 804.277 (m−1, due to loss of a proton to alleviate the dual positive charge) (FIG. 4).

Example 1.8: IR-1061-acridinium BArF Synthesis

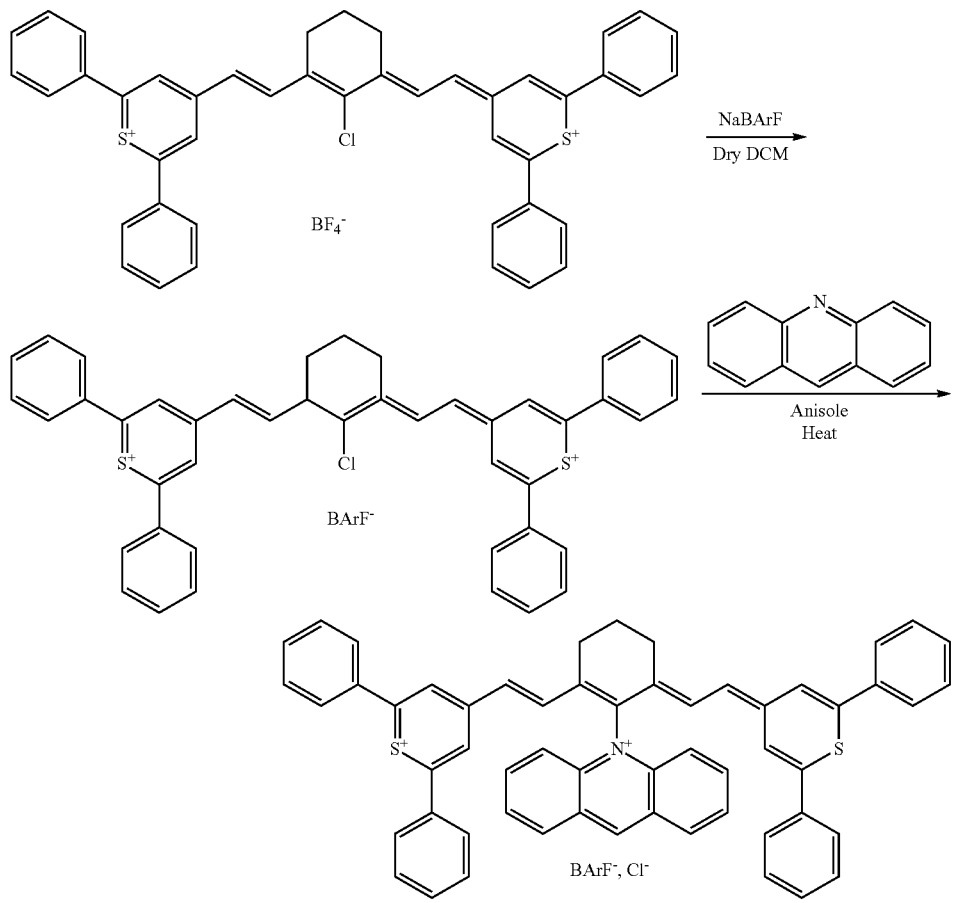

IR-1061 BarF⁻ was synthesized and purified in the manner previously described. Following isolation, 25 mgs of IR-1061 BArF (1 equivalent) was added to a 10 ml round-bottom flask along with a stir bar and 29.3 mgs of acridine (10 equivalents). Two milliliters of anisole were added, and the reaction was heated under argon. It was removed from heat once the color change from red to a yellow hued brown. Further heating led to formation of a green decomposition product. The reaction mixture was taken up in DCM and extracted three times with water and once with brine. The DCM fraction was pumped to near dryness, then resuspended in DCM and loaded onto a silica gel column. The product was eluted with a 0-1% MeOH in DCM gradient. 12 mgs of pure product were collected as a brown-yellow compound, giving a percent yield of 43%. NMR and mass spec data matched that of IR-1061-acridinium tetrafluoroborate, although significant peak broadening was observed on the MALDI with the BArF counterion. $^1$H-NMR: 7.75 (m, 2H), 7.68-7.60 (m, 12H), 7.52-7.42 (m, 14H), 6.99 (t, 2H) 6.91 (d, 2H), 6.65 (t, 2H), 6.59 (d, 2H), 6.28 (m, 1H), 2.84 (t, 2H), 2.56 (t, 2H), 1.95 (m, 2H) MS (MALDI): (m/z) calculated for $C_{57}H_{42}NS_2+$: 804.275 (m−1). Observed 804.5 (m−1, due to loss of a proton to alleviate the dual positive charge.

Example 2: Results

Heptamethine dyes present an opportune starting point for charge-transfer capable NIR dyes. A diverse class of chromophores, their solubility and absorption spectra can be significantly modified by altering the backbone termini. Furthermore, many contain an accessible backbone chlorine that can be used for introduction of a charge-transfer partner. Of the heptamethine dyes, the thiopyrilium dye IR-1061 was chosen for initial experiments due to its NIR absorption spectrum. Computation was used to rationally select an appropriate charge-transfer partner for IR-1061.

Figure 5:
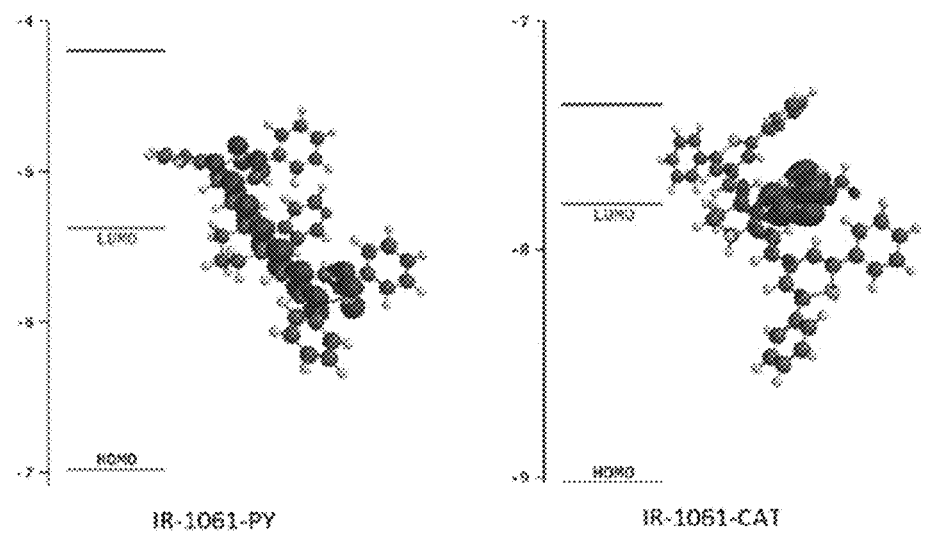
FIG. 5 illustrates several charge-transfer state computational predictions. For all molecules the HOMO resides on the primary chromophore and the LUMO is shown. A comparison of IR-1061-PY and IR-1061-CAT showing a similar orbital shift.
Figure 5:
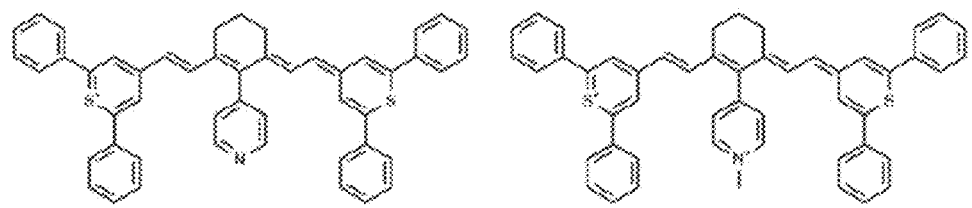

Initial work was done using a set of IR-1061 derivatives: cited herein as IR-1061-PY and IR-10161-CAT (FIG. 5).

Figure 6:
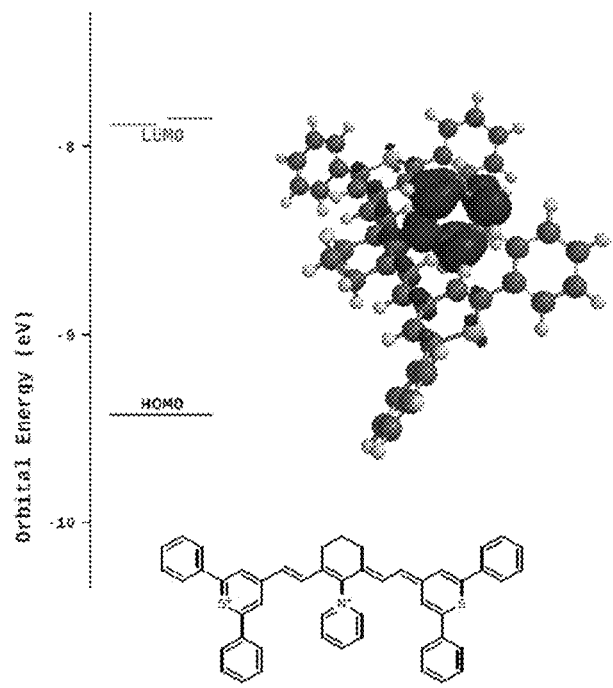
FIG. 6 illustrates IR-1061-pyridinium orbital energies. Upon inverting the pyridine charge-transfer partner so that it is linked via an N—C bond instead of a C—C bond, similar orbitals are observed. As in IR-1061-CAT, the HOMO resides on the heptamethine backbone.

In IR-1061-PY, both the HOMO and the LUMO remained on the heptamethine backbone, suggesting that no charge-transfer would occur. In IR-1061-CAT, the LUMO shifted to the N-methylpyridinium, generating a disjoint set of frontier molecular orbitals and suggesting that charge-transfer was possible. These results suggested that pyridinium might be a good starting point for an IR-1061 charge-transfer dye. To complement these results, an N—C linked dyad, called IR-1061-pyridinium (see Example 1.5 for structure), was also evaluated. The frontier orbitals remained disjoint, however, the LUMO and the LUMO$^{+1}$ were significantly closer in energy (FIG. 6).

Figure 7:
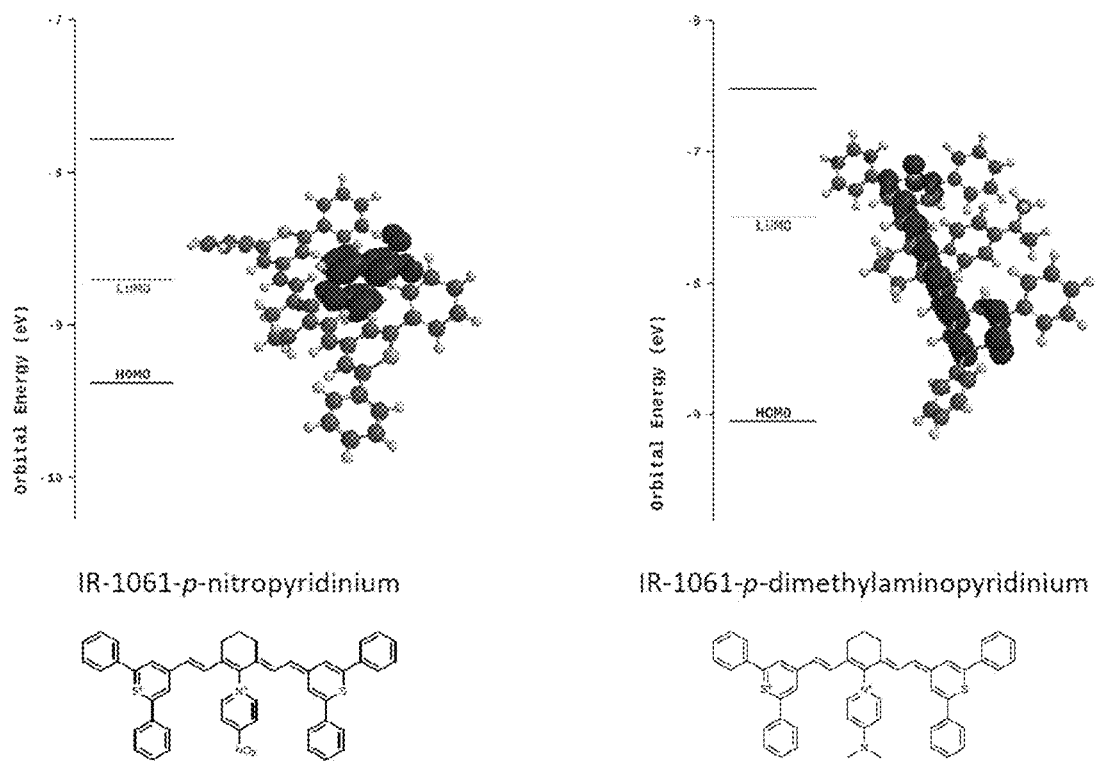
FIG. 7 illustrates representative IR-1061-pyridinium derivatives with electron withdrawing (p-nitro) and electron donating (p-dimethylamino) groups. Electron withdrawing groups reinforce frontier orbital orthogonality while electron donating groups do the opposite.

Since the N—C linkage in IR-1061-pyridinium provided an opportunity for functionalization at the pyridine 4-position, a number of derivatives were explored. Electron withdrawing groups tended to reinforce the observed disjoint character, whereas electron donating groups did the opposite, at times undoing the effect all together (FIG. 7).

Figure 8:
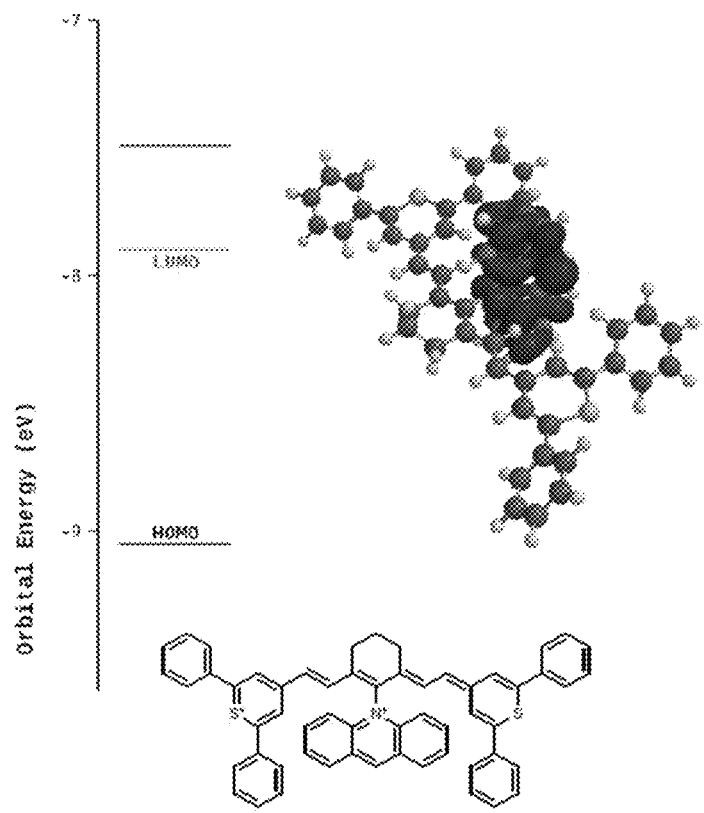
FIG. 8 illustrates IR-1061-acridinium orbital energies. In IR-1061-acridinium the orthogonal orbital is heavily favored as the LUMO, suggesting the possibility of charge-transfer. From the range of charge-transfer partners computationally vetted, IR-1061-pyridinium was selected for initial photochemical studies due to its synthetic accessibility.
Figure 9:
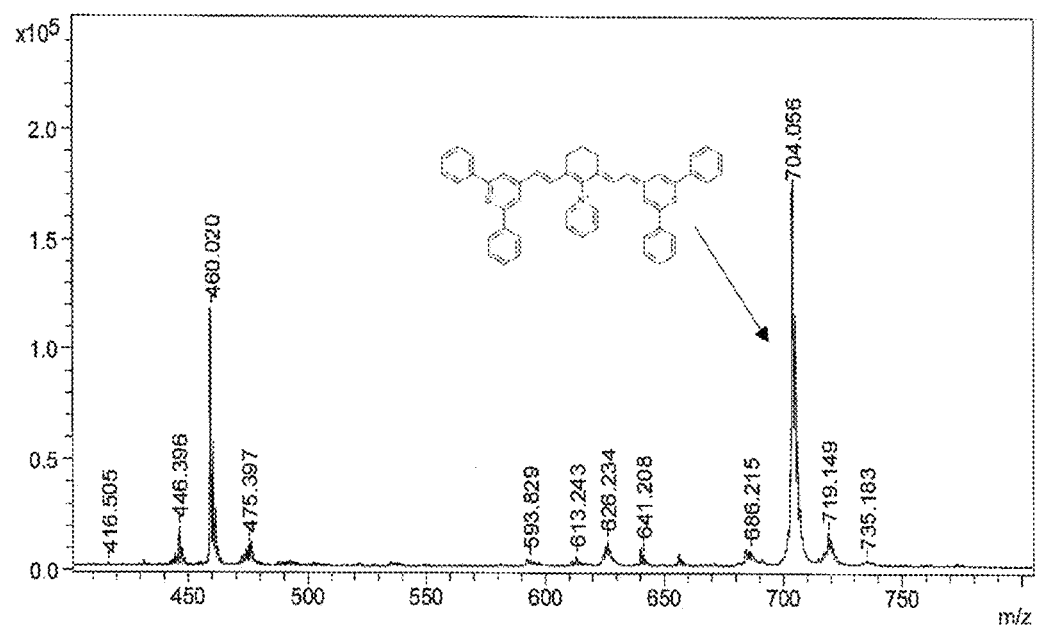
FIG. 9 illustrates MALDI of slightly impure IR-1061 pyridinium. When isolated, the major impurity at 460 amu has no absorbance in the NIR.
Figure 10A:
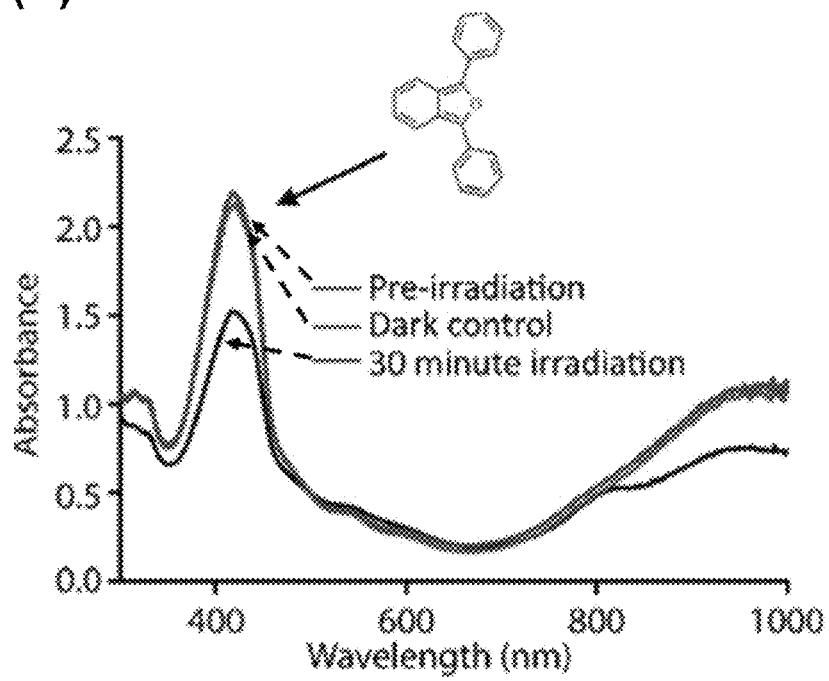
FIG. 10(A) illustrates the results of irradiation of IR-1061-pyridinium with DPBF. The structure of DPBF is shown next to its absorbance peak.
Figure 10B:
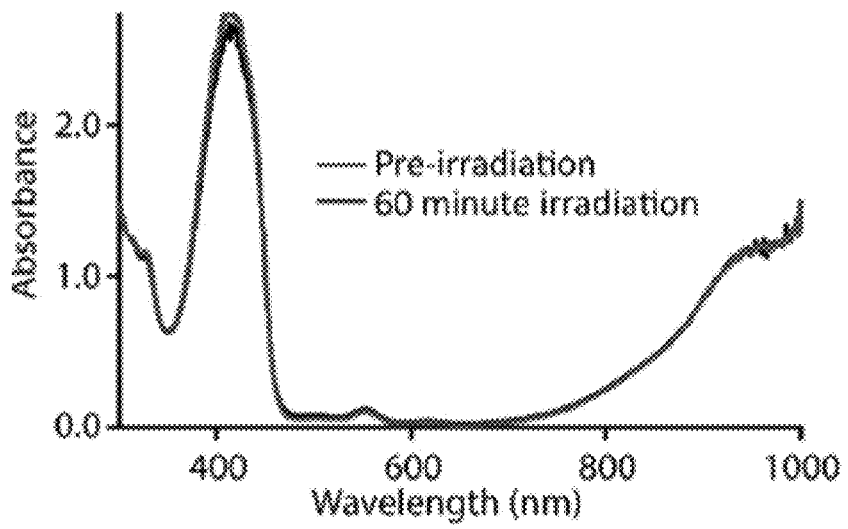
FIG. 10(B) illustrates the results of irradiation of IR-1061 with DPBF.

Beyond pyridine derivatives, a range of results were observed with different charge-transfer partners, with acridinium standing out as a potential alternative to pyridinium (FIG. 8). IR-1061-CAT was also considered, but its synthesis proved to be more challenging. The pyridine addition reaction was extremely sensitive to water, but gave good conversion using dry pyridine. Unfortunately, the product was too sensitive to isolate in pure form due to hydration that occurred under all evaluated purification conditions (FIG. 9). Despite this inconvenience, the slightly impure dye was used as a proof of principle. For initial singlet oxygen generation experiments, the dye was dissolved in $CDCl_3$—the solvent in which it had the highest solubility—and irradiated using a 1 $Wcm^{-2}$ 980 nm laser in the presence of a singlet oxygen trap, diphenylisobenzofuran (DPBF). DPBF was selected as a trap because it is a standard in the field and because other popular detectors (such as singlet oxygen sensor green, SOSG) led to precipitation of IR-1061-pyridinium over time. After 30 minutes of irradiation, a significant decrease in the DPBF signal was observed relative to a dark control, suggesting that singlet oxygen sensitization was occurring (FIG. 10(A)). In comparison, the parent dye, IR-1061, was irradiated under the same conditions and no significant changes in DPBF signal were observed (FIG. 10(B)). This suggested that the designed dye had novel reactivity at previously inaccessible wavelengths, but further characterization was required.

Figure 11:
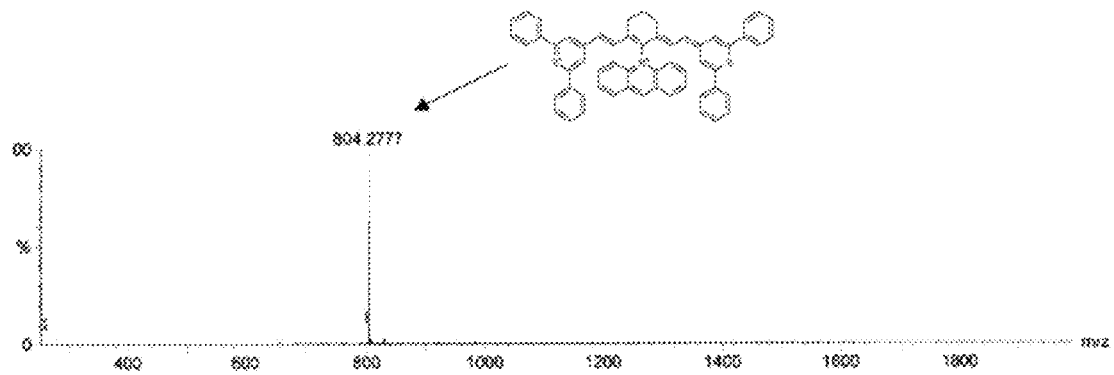
FIG. 11 illustrates ESI/TOF of IR-1061-acridinium
Figure 12:
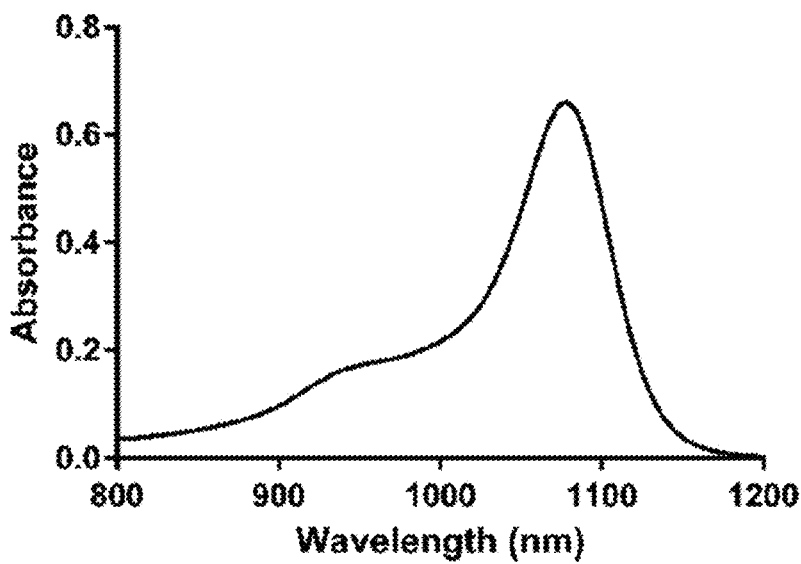
FIG. 12 illustrates NIR absorbance of IR-1061-acridinium in $CDCl_3$ at a concentration of 0.025 mg/ml (27 mM). $\lambda$max occurs at 1078, with a significant tail suggesting possible aggregation.

In an attempt to overcome the susceptibility of IR-1061-pyridinium to hydration, the pyridine charge-transfer partner was exchanged for acridine, which was expected to shield the dye from water addition due to its additional bulk. Although high temperatures—and thus a solvent with a high boiling point—were required to synthesize the derivative (Example 1.7), the product was more amenable to purification, ultimately yielding pure dye (FIG. 11). The absorption spectra of IR-1061-acridinium in chloroform was taken, and notably had significant tailing in the NIR (FIG. 12).

Figure 13:
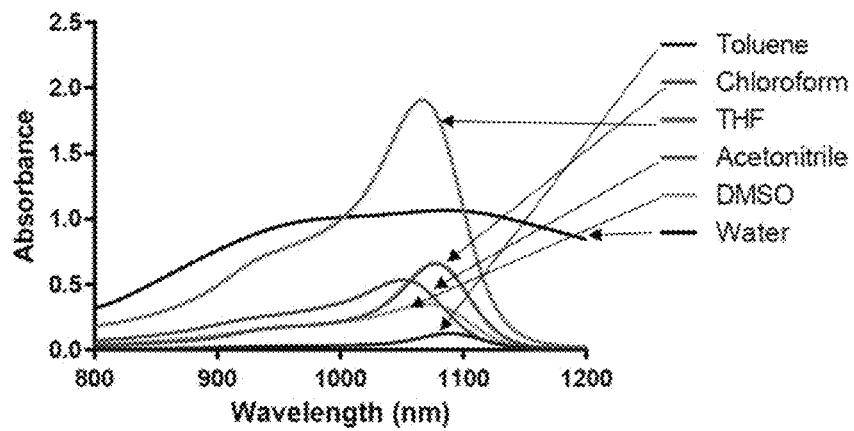
FIG. 13 shows absorption spectra of IR-1061-acridinium in different solvents at a concentration of 0.025 mg/ml. Most notable are the high extinction coefficient in THF and the extremely broad absorption spectrum in water.
Figure 14A:
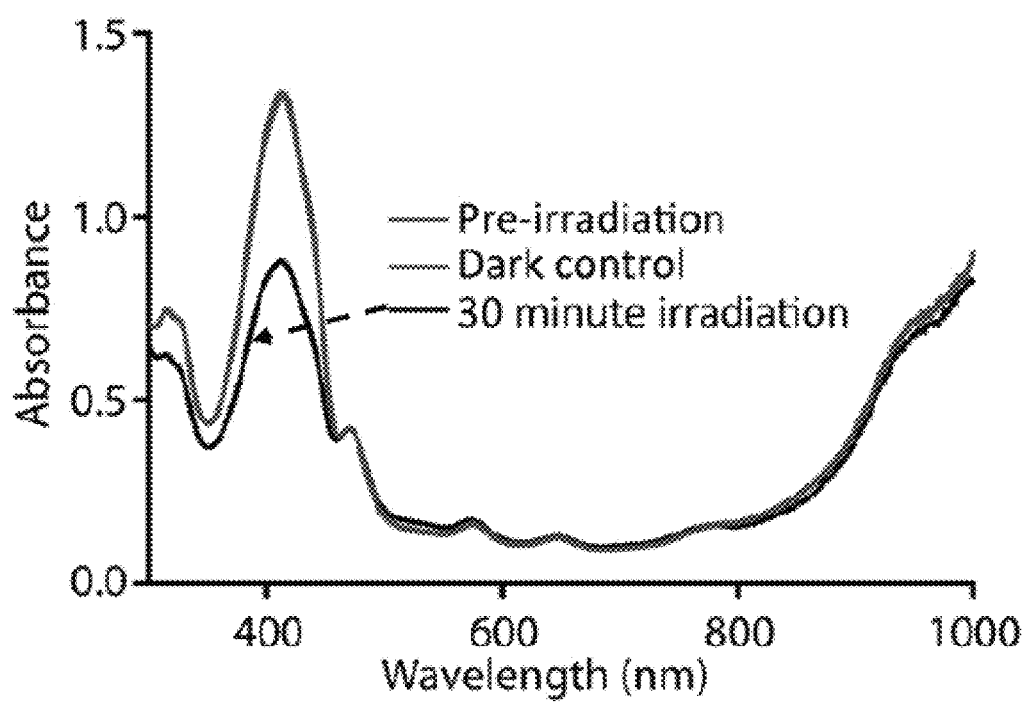
FIG. 14(A) illustrates results of irradiating IR-1061-acridinium with DPBF at 980 nm in $CDCl_3$.
Figure 14B:
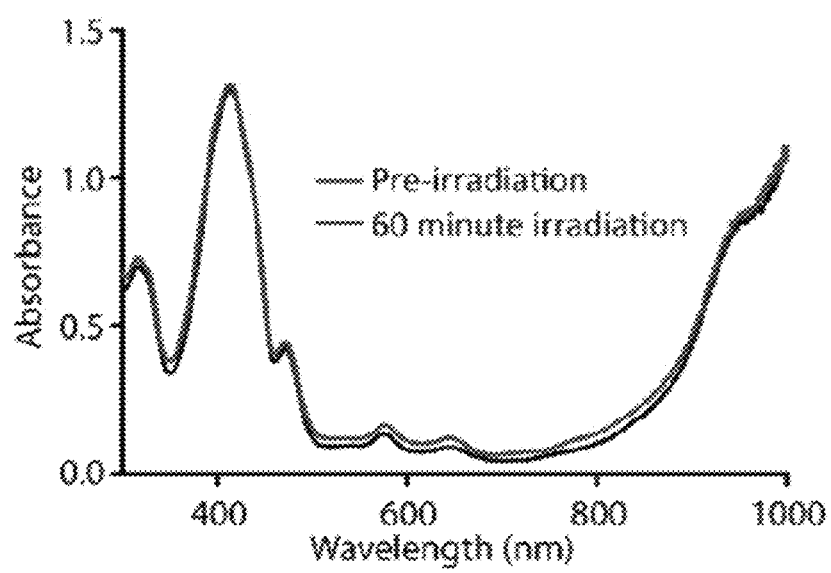
FIG. 14(B) illustrates results of irradiating IR-1061-acridinium with DPBF at 980 nm in freeze-pump-thawed $CDCl_3$.
Figure 14C:
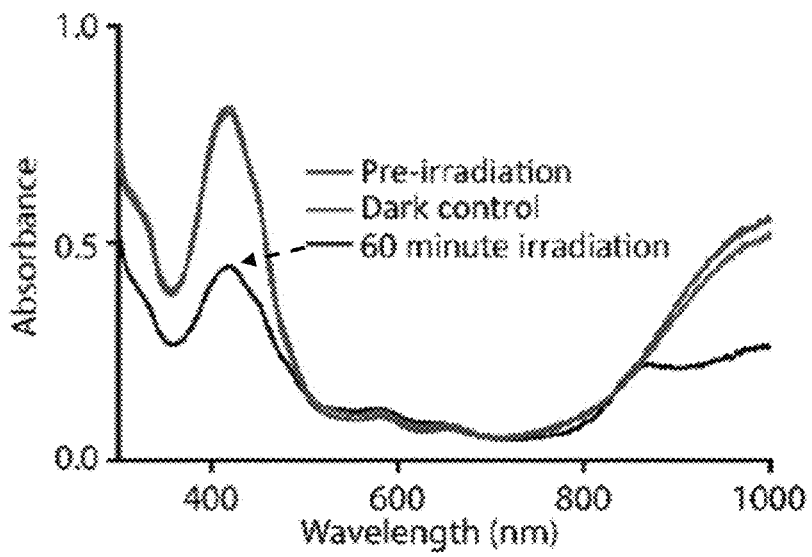
FIG. 14(AC) illustrates results of irradiating IR-1061-acridinium at 980 nm in $D_2O$ (with 7.5% DMSO-D6 for solubility).
Figure 15:
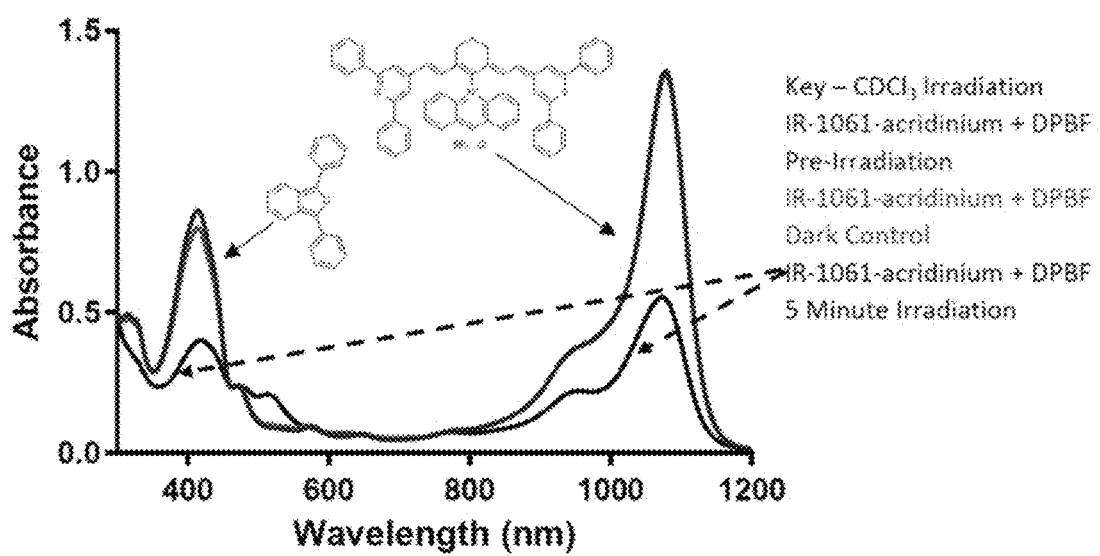
FIG. 15 illustrates results of irradiation experiments with IR-1061 with DPBF in $CDCl_3$ at 1064 nm.
Figure 16:
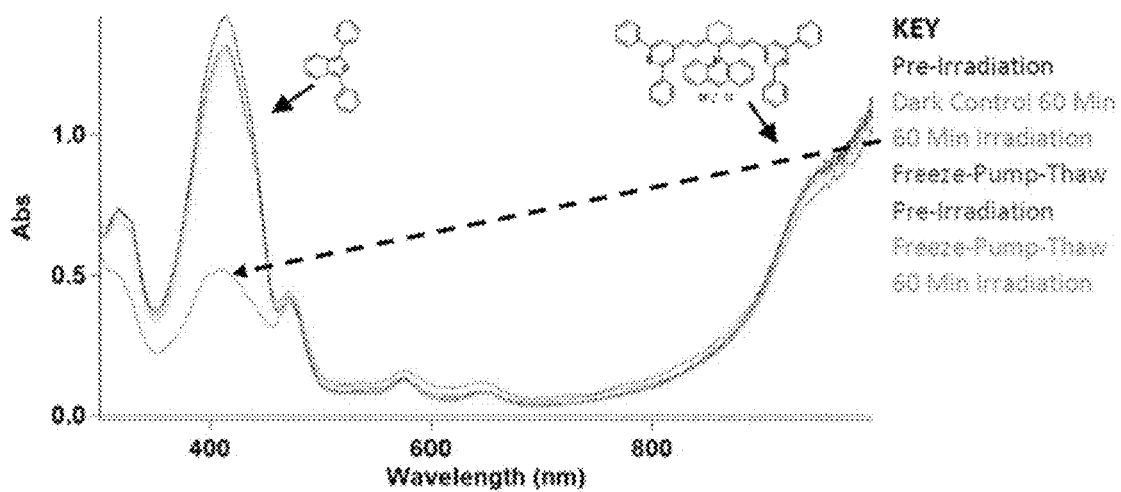
FIG. 16 illustrates results of irradiation of IR-1061-acridinium at 1064 nm in $CDCl_3$. Rapid bleaching of both the dye and DPBF signal was observed during irradiation.
Figure 17:
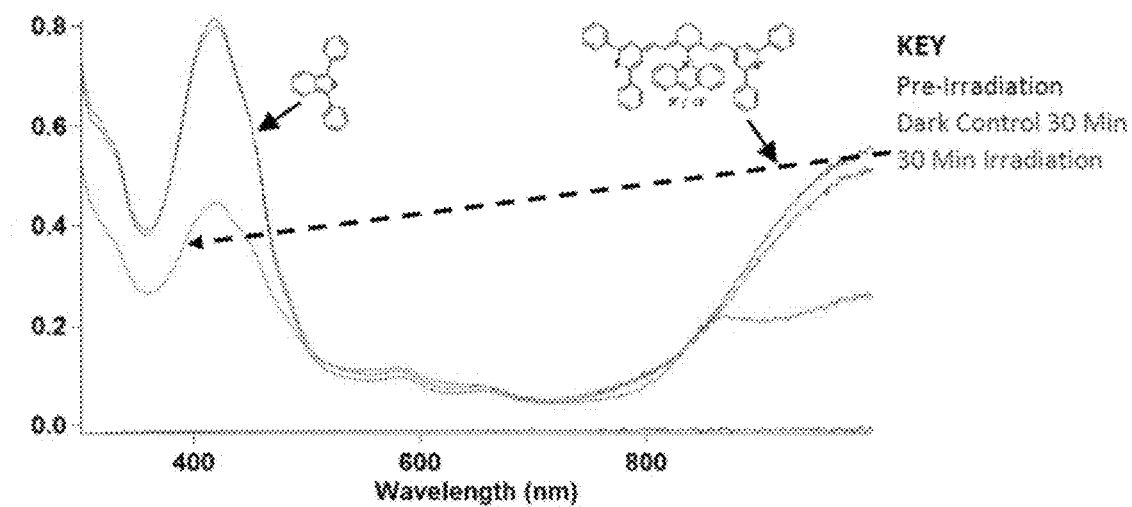
FIG. 17 illustrates results of IR-1061-acridinium irradiation experiments at 980 nm in 15% $D_6$-DMSO in deuterated water.

This phenomenon was reminiscent of spectra observed for other heptamethine dyes such as indocyanine green (ICG), which is known to demonstrate spectral shifting due to aggregation. To determine whether or not this phenomenon was specific to chloroform, the absorption spectra were taken in a range of solvents, (FIG. 13). In most, the dye had a similar spectrum, however, significant peak broadening was observed in water. Like IR-1061-pyridinium, IR-1061-acridinium was irradiated in $CDCl_3$ in the presence of DPBF using a 1 W $cm^{-2}$ 980 nm laser (FIG. 14(A)). As a comparison, a similar irradiation was carried out using a 1.8 W $cm^{-2}$ 1064 nm laser (FIG. 15). The collective effect of irradiation wavelength and conditions are seen in FIGS. 14(A-C), and FIGS. 15-18.

Figure 19:
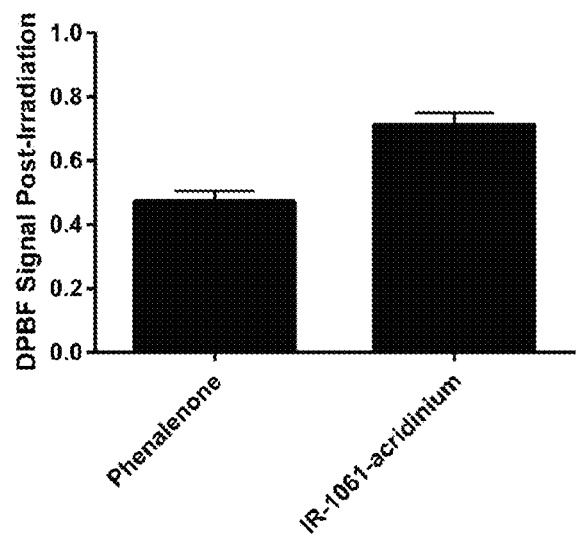
FIG. 19 illustrates normalized decrease in DPBF signal following irradiation in the presence of phenalenone and IR-1061-acridinium. An approximately 200-fold greater photon flux was used to irradiate IR-1061-acridinium.

Under both irradiation conditions, a decrease in DPBF signal was observed, however, the time scales varied drastically. At 980 nm significant DPBF photobleaching was observed only after 30 minutes, but in just 5 minutes of irradiation at 1064 nm, near complete photobleaching of DPBF was observed, as well as significant bleaching of the dye. This destruction of the dye is to be expected in the presence of high concentrations of singlet oxygen, as heptamethine dyes have been used as photoremovable protecting groups on the basis of this phenomenon. In an attempt to better define the efficiency of singlet oxygen generation, a relative quantum yield was obtained by comparing DPBF bleaching in the presence of IR-1061-acridinium and in the presence of phenalenone, a compound with a high quantum yield for singlet oxygen generation on irradiation at 365 nm in chloroform (FIG. 19).

Figure 18:
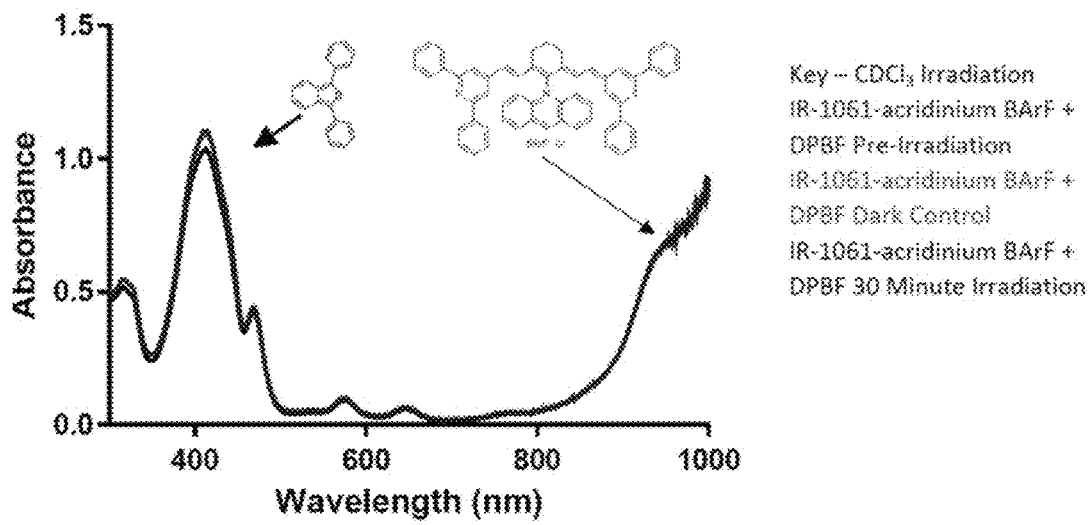
FIG. 18 illustrates results of irradiation of IR-1061-acridinium BArF at 980 nm in $CDCl_3$. Reactivity was significantly reduced upon exchanging the tetrafluoroborate counterion for a BArF counterion.

The results gave a relative quantum yield of 0.3%, which must be considered approximate given the substantially different wavelengths involved. Although this value was low, it provided a starting point for 1064 nm photochemistry and a benchmark for future generations of dyes. Further characterization of the dye was pursued at 980 nm, as it was a more controlled system. To confirm that the process was singlet oxygen-mediated, irradiation of a freeze-pump-thawed sample—devoid of oxygen—was carried out. This irradiation produced no change in DPBF signal (FIG. 14(B)), consistent with the idea that the process was singlet oxygen mediated. To evaluate the scope of the reaction, the dye was irradiated in an array of deuterated solvents. In nonpolar solvents, such as toluene, no singlet oxygen generation was observed. In polar aprotic solvents, such as DMSO, irradiation of the dye led to decreased DPBF degradation as well as photobleaching. In water, DPBF degradation rates comparable to those seen in chloroform were accompanied by high levels of photobleaching (FIG. 14(C)). Strong acids and bases both led to dye instability and bleaching prior to irradiation, and introduction of protein (in the form of BSA) led to precipitation of the dye. Exchanging the counterion from $BF4^-$ to $BarF^-$ resulted in an increase in solubility, but also a marked decrease in photosensitization capability (FIG. 18).

Recognizing that both the dye and the photosensitization process are sensitive, the generation of a dye capable of any photochemistry past 900 nm was a significant achievement and marked a first in the field. The reactivity of both IR-1061-pyridinium and IR-1061-acridinium support the design principles used to conceptualize the dyes as well as the predictive value of the performed calculations.

Each patent, patent application, and publication cited or described in this document is hereby incorporated herein by reference, each in its entirety, for all purposes, or at least for the purposes or in the context where it was cited.

What is claimed:

1. A compound that is a near-infrared (NIR) absorbing dye, wherein the compound is

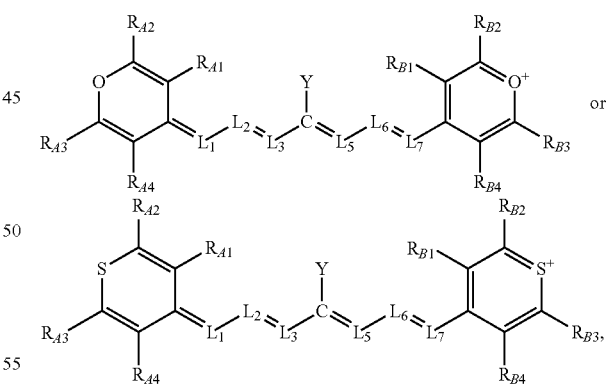

or a rotational or conformational isomer or a salt thereof; wherein $L_1$, $L_2$, $L_3$, $L_5$, $L_6$, and $L_7$ are substituted or unsubstituted methines, wherein the optional substituents are independently $C_{1-6}$ alkyl or $C_{2-6}$ alkenyl; or $L_1$ and $L_3$, or $L_3$ and $L_5$, or $L_5$ and $L_7$ may be linked with $C_{2-4}$ alkylene or $C_{2-4}$ alkenylene substituents;

$R_{A1}$, $R_{A2}$, $R_{A3}$, $R_{A4}$, $R_{B1}$, $R_{B2}$, $R_{B3}$, and $R_{B4}$ are each independently H, deuterium, or tritium, an $C_{1-12}$ alkyl, —[$CH_2$—$CH_2$—O-]$_{1-6}R^{10}$, $C_{2-12}$ alkenyl, polyglycol, optionally substituted 5- or 10-membered aryl or heteroaryl group, halo, nitro, cyano, —(C$_{0-12}$alkyl) sulfonate or a salt thereof, —(C$_{0-12}$alkyl) sulfate or a salt thereof, —(C$_{0-12}$alkyl)phophate or a salt thereof, —(C$_{0-12}$alkyl)hydroxy, —(C$_{0-12}$alkyl)alkoxy, —(C$_{0-12}$alkyl)aryloxy, —(C$_{0-12}$alkyl)NHSO$_3$R$_{10}$ or a salt thereof, —(C$_{0-12}$alkyl)COOR$^{10}$ or a salt thereof, —(C$_{0-12}$alkyl)CON(R$^{10}$)$_2$, —(C$_{0-12}$alkyl)N(R$^{10}$)$_2$ or a salt thereof, or —(C$_{0-12}$alkyl)borate;

is independently 0, 1, 2, 3, or 4;

R$^{10}$ is independently H or C$_{1-6}$ alkyl; and

Y is an optionally substituted cationic heteroaryl ring moiety.

2. The compound of claim 1, wherein the methines not bonded to Y are otherwise not substituted.

3. The compound of claim 1, wherein the compound is

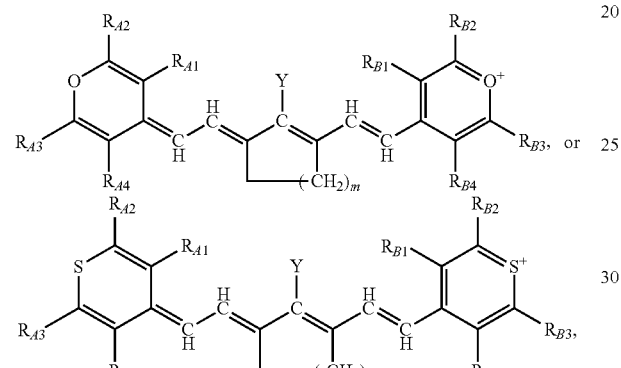

or a rotational or conformational isomer or a salt thereof; where m is 1, 2, or 3; Y is an optionally substituted cationic heteroaryl ring moiety; and wherein R$_{A1}$, R$_{A4}$, R$_{B1}$, and R$_{B4}$ are H, or an isotope thereof, and R$_{A2}$, R$_{A3}$, R$_{B2}$, and R$_{B3}$ are aryl, heteroaryl, or branched alkyl.

4. The compound of claim 1, wherein the optionally substituted cationic heteroaryl ring moiety is an optionally substituted acridinium, benzoxazolium, benzothiazolium, imidazolium, isoxazolium, isoquinolinium, isothiazolium, naphthoimidazolium, naphthothiazolium, naphthoxazolium, oxazolium, pyrazinium, pyrazolium, pyridimium, pyridinium, quinolinium, tetrazinium, tetrazolium, thiazolium, triazinium, triazolium, benzopyrazinium, benzopyridimium, benzopyridinium, naphthopyrazinium, naphthopyridimium, benzopyridinium, benzotriazinium, naphthotriazinium moiety, pyrylium chromenylium xanthylium thiopyrylium thiochromenylium or thioxanthylium moiety.

5. The compound of claim 1, wherein the optionally substituted cationic heteroaryl ring moiety is a structure:

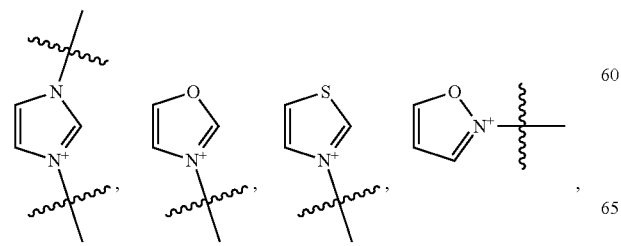

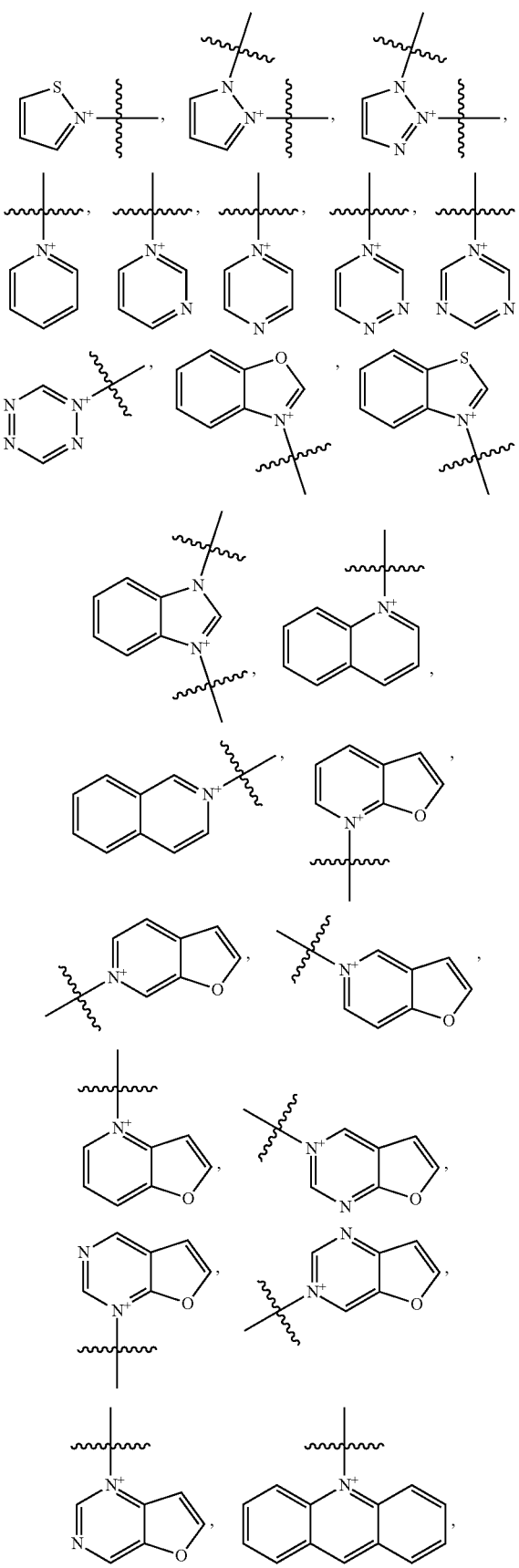

53

-continued

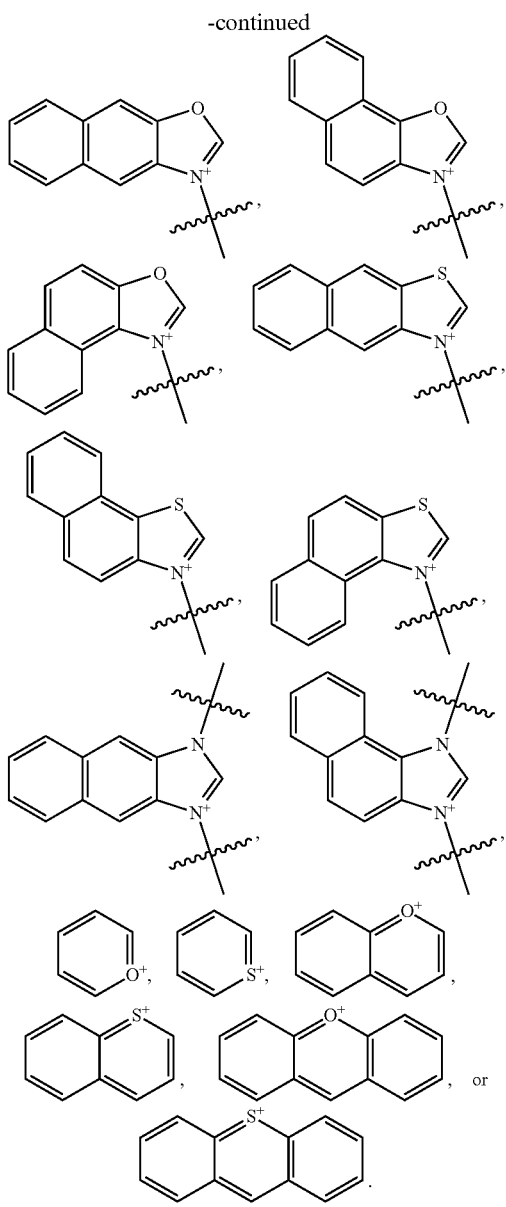

6. The compound of claim 1, wherein at least one associated cationic group or moiety is charge balanced by a halide ion, perchlorate, tetrafluoroborate, hexafluorophosphate, sulfate, hydrogensulfate, nitrate, trifluoroacetate, trichloroacetate, triflate, mesylate, and/or p-toluenesulfonate ion.

7. The compound of claim 1, wherein the compound comprises, is substituted with, or is conjugated to at least one element enriched in an isotope of carbon, chlorine, fluorine, hydrogen, iodine, nitrogen, or oxygen above its natural abundance.

8. The compound of claim 1, that exhibits a local $\lambda_{max}$ for light absorption in a range of from 750 nm to 1400 nm.

9. The compound of claim 1, that generates singlet oxygen, when the compound is irradiated in the presence of $O_2$ at a wavelength in a range of from 750 nm to 1400 nm.

10. A composition comprising a compound of claim 1, dissolved in or suspended in or in contact with a solvent comprising a deuterated solvent.

11. An optical filter comprising a transparent support comprising a polymer film and at least one filter layer, wherein the filter layer contains a compound of claim 1.

12. The compound of claim 1, wherein the compound is:

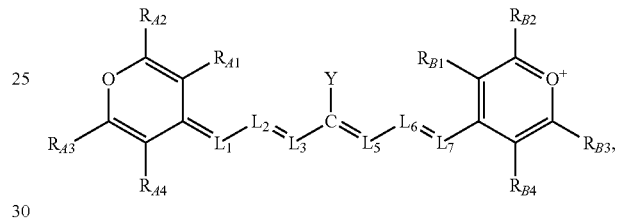

or a rotational or conformational isomer or a salt thereof.

13. The compound of claim 1, wherein the compound is:

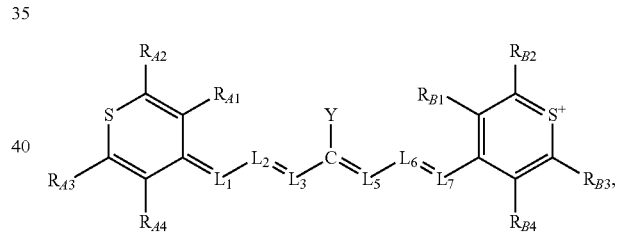

or a rotational or conformational isomer or a salt thereof.

14. The compound of claim 3, wherein $R_{A2}$, $R_{A3}$, $R_{B2}$, and $R_{B3}$ are phenyl, pyridinyl, or tert-butyl.

* * * * *